(12) United States Patent
Nagamatsu et al.

(10) Patent No.: US 10,905,828 B2
(45) Date of Patent: Feb. 2, 2021

(54) ADMINISTRATION APPARATUS DESIGN SYSTEM, ADMINISTRATION SYSTEM, ADMINISTRATION APPARATUS DESIGN METHOD, ADMINISTRATION APPARATUS DESIGN PROGRAM, AND MEDICAL APPARATUS DESIGN SYSTEM

(71) Applicant: DAICEL CORPORATION, Osaka (JP)

(72) Inventors: Shinji Nagamatsu, Osaka (JP); Shingo Oda, Osaka (JP); Toru Kitaguchi, Osaka (JP); Shinichi Kawamura, Tokyo (JP); Naoto Okuyama, Hyogo (JP); Masashi Iwayama, Hyogo (JP)

(73) Assignee: Daicel Corporation, Osaka (JP)

( * ) Notice: Subject to any disclaimer, the term of this patent is extended or adjusted under 35 U.S.C. 154(b) by 176 days.

(21) Appl. No.: 16/022,430

(22) Filed: Jun. 28, 2018

(65) Prior Publication Data
US 2018/0369484 A1    Dec. 27, 2018

Related U.S. Application Data

(63) Continuation of application No. PCT/JP2016/089188, filed on Dec. 28, 2016.

(30) Foreign Application Priority Data

Dec. 28, 2015 (JP) ................... 2015-255801

(51) Int. Cl.
*A61M 5/20* (2006.01)
*A61M 5/30* (2006.01)
(Continued)

(52) U.S. Cl.
CPC ............ *A61M 5/2046* (2013.01); *A61M 5/30* (2013.01); *A61M 5/3129* (2013.01); *G16H 20/17* (2018.01);
(Continued)

(58) Field of Classification Search
CPC .... A61M 5/2046; A61M 5/30; A61M 5/3129; A61M 2005/3132; A61M 5/46; G16H 40/63; G16H 20/17
See application file for complete search history.

(56) References Cited

U.S. PATENT DOCUMENTS 6,936,303 B1    8/2005 Katsuda et al.
8,133,494 B2    3/2012 zur Megede et al.
(Continued)

FOREIGN PATENT DOCUMENTS

JP    2003-025950 A    1/2003
JP    2003-261777 A    9/2003
(Continued)

OTHER PUBLICATIONS

International Search Report and Written Opinion dated Mar. 14, 2017 in related International Application No. PCT/JP2016/089194.
(Continued)

*Primary Examiner* — Amber R Stiles
(74) *Attorney, Agent, or Firm* — Knobbe Martens Olson & Bear LLP

(57) ABSTRACT

Provided is a system for calculating design specifications of an administration apparatus which administers an administration object substance to an object region using a high-energy substance as a driving source. An object administration apparatus to be an object of calculation of the design specifications is specified and substance information related to a prescribed administration object substance to be administered in the object administration apparatus is acquired. Region information related to a prescribed object region is acquired, and distribution information related to a distribution state of the prescribed administration object substance is acquired. In addition, based on the respective pieces of acquired information, design specification information related to a configuration of the object administration appa-
(Continued)

ratus including energy information related to a high-energy substance to be used to administer the prescribed administration object substance is calculated. Accordingly, convenience of the administration apparatus is improved.

18 Claims, 10 Drawing Sheets

(51) Int. Cl.
*A61M 5/31* (2006.01)
*G16H 40/63* (2018.01)
*G16H 20/17* (2018.01)
*A61M 5/46* (2006.01)

(52) U.S. Cl.
CPC ............... *G16H 40/63* (2018.01); *A61M 5/46* (2013.01); *A61M 2005/3132* (2013.01)

(56) References Cited

U.S. PATENT DOCUMENTS

| | | | |
|---|---|---|---|
| 2002/0174792 A1 | 11/2002 | Kubozuka et al. | |
| 2003/0149396 A1 | 8/2003 | Alexandre et al. | |
| 2004/0035491 A1 | 2/2004 | Castellano | |
| 2004/0133150 A1 | 7/2004 | Hjertman et al. | |
| 2005/0027239 A1 | 2/2005 | Stout et al. | |
| 2006/0281175 A1 | 12/2006 | McSwiggen et al. | |
| 2008/0132450 A1 | 6/2008 | Lee et al. | |
| 2010/0040619 A1 | 2/2010 | Li et al. | |
| 2012/0089114 A1* | 4/2012 | Hemond | A61M 5/30 604/500 |
| 2013/0237951 A1 | 9/2013 | Oda | |
| 2013/0304017 A1* | 11/2013 | Williamson | A61M 5/484 604/500 |
| 2014/0012226 A1 | 1/2014 | Hochman | |
| 2015/0032082 A1 | 1/2015 | Kudoh | |
| 2018/0036485 A1 | 2/2018 | Oda | |
| 2018/0056003 A1 | 3/2018 | Oda | |

FOREIGN PATENT DOCUMENTS

| | | |
|---|---|---|
| JP | 2005-021640 A | 1/2005 |
| JP | 2005-523679 A | 8/2005 |
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2012-061269 A | 3/2012 |
| JP | 2012-065920 A | 4/2012 |
| JP | 2013-059424 A | 4/2013 |
| WO | WO 01/031282 A1 | 5/2001 |
| WO | WO 2004/011066 A1 | 2/2004 |
| WO | WO 2012/039454 A1 | 3/2012 |

OTHER PUBLICATIONS

International Search Report and Written Opinion dated Mar. 14, 2017 in related International Application No. PCT/JP2016/089190.
International Search Report and Written Opinion dated Mar. 14, 2017 in related International Application No. PCT/JP2016/089188.
Extended European Search Report dated Jul. 30, 2019 in European Application No. 16881841.7, in 12 pages.
Extended European Search Report dated Nov. 11, 2019 in related European Application No. 16881842.5, in 12 pages.
Extended European Search Report dated Jul. 31, 2019 in related European Application No. 16881843.3, in 18 pages.
Office Action dated Apr. 16, 2020 in related U.S. Appl. No. 16/022,487, in 15 pages.
Office Action dated Apr. 16, 2020 in related U.S. Appl. No. 16/022,471, in 17 pages.

* cited by examiner

ADMINISTRATION APPARATUS DESIGN SYSTEM, ADMINISTRATION SYSTEM, ADMINISTRATION APPARATUS DESIGN METHOD, ADMINISTRATION APPARATUS DESIGN PROGRAM, AND MEDICAL APPARATUS DESIGN SYSTEM

CROSS-REFERENCE TO RELATED APPLICATIONS

This application is a continuation application, and claims the benefit under 35 U.S.C. §§ 120 and 365 of PCT Application No. PCT/JP2016/089188, filed on Dec. 28, 2016, which is hereby incorporated by reference. PCT/JP2016/089188 also claimed priority from Japanese Patent Application No. 2015-255801 filed on Dec. 28, 2015, the entire contents of which are incorporated by reference.

TECHNICAL FIELD

The described technology relates to a system for calculating design specifications of an administration apparatus which administers an administration object substance such as a drug solution to an object region using a high-energy substance as a power source.

BACKGROUND ART

While an injector can be exemplified as an apparatus for administering a drug solution to an object region such as a living organism, needle-free injectors without a needle have been developed in recent years from the perspectives of handleability, hygiene, and the like. Generally, with respect to a needle-free injector, a configuration has been put to practical use in which a drug solution pressurized by a driving source such as compressed gas or a spring is injected toward an object region and the drug solution is administered inside the object region using kinetic energy of the drug solution. Further, the use of powder combustion is being studied as an alternative driving source. As described above, since a needle-free injector does not have a mechanical construction (for example, a needle) which comes into direct contact with the inside of the object region, needle-free injectors are highly convenient for a user. On the other hand, precisely due to the absence of such a mechanical construction, it is not necessarily easy to administer a drug solution to a desired site within an object region.

PTL 1 discloses a technique for feeding a drug solution to a desired depth of a skin structure of a living organism using a needle-free injector. Specifically, with respect to pressurization for injection of an injection solution, in order to form a through-passage in an injection object region, pressurization control is carried out which involves performing: a first pressurization mode in which, after pressure is raised to first peak pressure, pressure to the injection solution is lowered to stand-by pressure; and a second pressurization mode in which the injection solution at the stand-by pressure is pressurized to raise the pressure to the injection solution to second peak pressure and a prescribed injection amount is injected. Performing such pressurization control controls behavior of the injection solution in the object region.

SUMMARY

Problems to be Solved

Previously, in various administration apparatuses including needle-free injectors, a spring, compressed gas, gunpowder, and the like have been used as a driving source for administration. The inventors of the described technology focused on high-energy substances including gunpowders and explosives as a driving source. Since energy generated by combustion of a high-energy substance is extremely large and a relatively large amount of an administration object substance can be pressurized with a small amount of a high-energy substance, high-energy substances are expected to improve administration capabilities of administration apparatuses. On the other hand, when administering an administration object substance to an object region, it is desired that the administration object substance be precisely administered to a specific site where the substance is expected to have efficacy and the like.

With the technique disclosed in Japanese Patent Application Laid-open No. 2012-61269, preferable injection of an injection solution is achieved by separately controlling pressure applied to the injection solution by powder combustion in two pressurization modes. However, since conditions related to an amount of the injection solution to be injected and a distribution or a diffusion of the injection solution in an object region are not always constant, the injection solution cannot necessarily be delivered to a desired site based solely on the disclosed technique. In addition, administration apparatuses include various apparatus such as catheters in addition to injectors including needle-free injectors, and a mode of administration of a substance to an object region differs from one apparatus to another. Therefore, the technique disclosed in Japanese Patent Application Laid-open No. 2012-61269 cannot necessarily be preferably applied to administration apparatuses other than needle-free injectors.

In consideration of the problem described above, an object of the described technology is to provide, in an administration apparatus which administers an administration object substance to an object region using a high-energy substance as a driving source, a technique for calculating design specification information related to a configuration of the administration apparatus including energy information related to the high-energy substance to improve convenience of the administration apparatus.

Example Means for Solving the Problems

In order to solve the problem described above, the described technology adopts a configuration in which design specification information related to a configuration of an administration apparatus is calculated based on information related to a substance to be administered, information related to an object region, and information related to an anticipated distribution of an administration object substance in the object region. Accordingly, since a user can readily obtain specifications of a high-energy substance as a driving source to be used in an administration apparatus and specifications related to a configuration of the administration apparatus associated with administration of an administration object substance, convenience of the administration apparatus can be preferably improved.

Specifically, the described technology is a system which calculates design specifications of an administration apparatus which administers an administration object substance to an object region using a high-energy substance as a driving source, the system including: an apparatus specification unit which specifies the administration apparatus to be an object of calculation of the design specifications, as an object administration apparatus; a first acquisition unit which acquires substance information related to a prescribed administration object substance to be administered in the object administration apparatus; a second acquisition unit which acquires region information related to a prescribed object region to which the prescribed administration object substance is to be administered; a third acquisition unit which acquires distribution information related to a distribution state of the prescribed administration object substance, the distribution state being anticipated to be formed in the prescribed object region when the prescribed administration object substance is administered by the object administration apparatus; and a calculation unit which calculates, based on the substance information acquired by the first acquisition unit, the region information acquired by the second acquisition unit, and the distribution information acquired by the third acquisition unit, design specification information related to a configuration of the object administration apparatus including energy information related to the high-energy substance to be used to administer the prescribed administration object substance.

With the administration apparatus design system according to the described technology, in an administration apparatus, design specification information related to a configuration of the administration apparatus necessary for administering an administration object substance to an object region using a high-energy substance as a power source is calculated by the calculation unit. In this case, high-energy substances are substances including gunpowders and explosives. In addition, substance information, region information, and distribution information are used for the calculation. These pieces of information are related to desired operations which a user hopes to be realized in an administration apparatus when the administration apparatus is driven using a high-energy substance as a driving source. Specifically, substance information refers to information related to a prescribed administration object substance which the user desires to administer, and examples thereof include a dose of the substance. In addition, region information refers to information related to the object region to which the administration object substance is to be administered and, when the substance is to be administered to a living organism, examples of region information include an organ of the living organism which corresponds to an administration location and hardness of the object region (difficulty of penetration by the administration object substance), and when the object region is a living organism, individual physical information (age, weight, race, and the like) of the living organism.

Furthermore, distribution information may be information including at least one of information related to an administration depth of the administration object substance in the object region and information related to a spread of the administration object substance in the object region. Information related to an administration depth refers to information indicating a degree at which the administration object substance penetrates in a vertical direction from a superficial layer of the object region desired by the user (in other words, a depth from the superficial layer of the object region desired by the user). In addition, information related to a spread of the administration object substance refers to information related to a spread of the administration object substance in the object region desired by the user.

In addition, the design specification information includes at least energy information related to the high-energy substance as a driving source and may further include information related to a configuration of the administration apparatus associated with administration of the administration object substance such as information related to a structure or a size of a space (a chamber) in which combustion of the high-energy substance takes place in the administration apparatus, information related to a structure or a size of a structure (for example, a piston) for transmitting energy generated by the combustion of the high-energy substance to the administration object substance, or information related to a structure or a size of a structure (for example, a nozzle) for administering the administration object substance to the object region.

In this case, when using combustion energy of a high-energy substance as a power source of an administration apparatus, examples of the high-energy substance include any one of gunpowder containing zirconium and potassium perchlorate, gunpowder containing titanium hydride and potassium perchlorate, gunpowder containing titanium and potassium perchlorate, gunpowder containing aluminum and potassium perchlorate, gunpowder containing aluminum and bismuth oxide, gunpowder containing aluminum and molybdenum oxide, gunpowder containing aluminum and copper oxide, gunpowder containing aluminum and iron oxide, and gunpowder consisting of a combination of a plurality thereof. With such high-energy substances, since a combustion product thereof characteristically does not have a gaseous component at normal temperature even though the combustion product is gaseous in a high-temperature state, as a result of the combustion product performing condensation immediately after ignition, using such a high-energy substance for administration to the object region enables efficient administration to shallower sites of the object region. In addition, information related to a type, a loaded amount, or the like of a high-energy substance which is usable in such an administration apparatus or, in other words, information related to a high-energy substance for realizing functions as a power source in the administration apparatus is considered the energy information described earlier and is included in the design specification information of the administration apparatus.

As described above, having the calculation unit calculate design specification information of an object administration apparatus specified by the apparatus specification unit based on substance information, region information, and distribution information or, in other words, design specification information of an administration apparatus which the user desires to use, the user can readily configure the administration apparatus to a usable state in accordance with a prescribed purpose and can further use the administration apparatus.

In addition, in the administration apparatus design system described above, the administration apparatus may be an apparatus which administers the administration object substance into the object region by injecting the administration object substance toward the object region using the high-energy substance as a power source and causing the administration object substance to penetrate a superficial layer of the object region, without involving an introduction unit which introduces the administration object substance into the object region. With such an administration apparatus, it is particularly difficult to administer the administration object substance into the object region in a manner desired by the user. However, in the system according to the described technology, calculating the design specification information enables the administration apparatus to be readily operated in a manner desired by the user and significantly improves convenience of the user.

The administration apparatus design system described heretofore may further include an object region sensor which detects a prescribed physical parameter related to hardness of the superficial layer of the prescribed object region, in which case the second acquisition unit may acquire, as at least a part of the region information, the prescribed physical parameter detected by the object region sensor. Using an object region sensor in this manner enables a prescribed physical parameter related to the hardness of the superficial layer of the prescribed object region as a piece of region information to be readily acquired and improves convenience of the user.

In addition, the administration apparatus design system described heretofore may further include a map information holding unit that holds a calculation map which corresponds to each of a plurality of types of the administration apparatus and which defines a correlation between the substance information, the region information and the distribution information, and the design specification information for each administration apparatus. In this case, the calculation unit calculates the design specification information based on a calculation map corresponding to the object administration apparatus specified by the apparatus specification unit, among the calculation maps held by the map information holding unit. Having a model information holding unit prepare a calculation map related to corresponding design specification information for each administration apparatus in this manner, design specification information in accordance with each administration apparatus can be appropriately calculated.

Furthermore, an administration system which includes the administration apparatus design system described heretofore and which is provided with: the administration apparatus which administers the administration object substance to the object region using the high-energy substance as a power source without involving an introduction unit; and a preparation apparatus which prepares a high-energy substance of a type and in a loaded amount that correspond to the object administration apparatus, in accordance with the energy information included in the design specification information calculated by the calculation unit also belongs to a scope of protection of the described technology. In the administration system, by using energy information included in design specification information calculated by the design system, a high-energy substance, the type and the loaded amount of which are compatible with the energy information and which corresponds to an administration apparatus that administers the administration object substance without involving an introduction unit, is to be prepared. As a result, preparation of an administration apparatus can be very readily achieved.

In addition, the described technology can also be perceived from an aspect of a method of calculating design specifications of an administration apparatus which administers an administration object substance to an object region using a high-energy substance as a power source. Specifically, the described technology is an administration apparatus design method including: an apparatus specification step of specifying the administration apparatus to be an object of calculation of the design specifications, as an object administration apparatus; a first acquisition step of acquiring substance information related to a prescribed administration object substance to be administered in the object administration apparatus; a second acquisition step of acquiring region information related to a prescribed object region to which the prescribed administration object substance is to be administered; a third acquisition step of acquiring distribution information related to a distribution state of the prescribed administration object substance, the distribution state being anticipated to be formed in the prescribed object region when the prescribed administration object substance is administered by the object administration apparatus; and a calculation step of calculating, based on the substance information acquired in the first acquisition step, the region information acquired in the second acquisition step, and the distribution information acquired in the third acquisition step, design specification information related to a configuration of the object administration apparatus including energy information related to the high-energy substance to be used to administer the prescribed administration object substance. Moreover, the technical concepts disclosed in relation to the administration apparatus design system described above can also be applied to the described technology as long as no technical inconsistencies arise.

Furthermore, the described technology can also be perceived from an aspect of a program which causes a processing apparatus to calculate design specifications of an administration apparatus which administers an administration object substance to an object region using a high-energy substance as a power source. Specifically, the described technology is an administration apparatus design program which causes the processing apparatus to execute: an apparatus specification step of specifying the administration apparatus to be an object of calculation of the design specifications, as an object administration apparatus; a first acquisition step of acquiring substance information related to a prescribed administration object substance to be administered in the object administration apparatus; a second acquisition step of acquiring region information related to a prescribed object region to which the prescribed administration object substance is to be administered; a third acquisition step of acquiring distribution information related to a distribution state of the prescribed administration object substance, the distribution state being anticipated to be formed in the prescribed object region when the prescribed administration object substance is administered by the object administration apparatus; and a calculation step of calculating, based on the substance information acquired in the first acquisition step, the region information acquired in the second acquisition step, and the distribution information acquired in the third acquisition step, design specification information related to a configuration of the object administration apparatus including energy information related to the high-energy substance to be used to administer the prescribed administration object substance. Moreover, the technical concepts disclosed in relation to the administration apparatus design system described above can also be applied to the described technology as long as no technical inconsistencies arise.

While the described technology described heretofore is related to an administration apparatus design system and the like, a system and the like which take more specific usage of an administration apparatus into consideration are also included in the scope of the described technology. Examples include an education support system for educating use of an administration apparatus to a user thereof at a site of use of the administration apparatus. It is difficult for the user to appropriately utilize the administration apparatus particularly in an initial stage of use. In consideration thereof, usage as an education support system of a user can also be described a mode of utilizing the technical concepts of the described technology in a meaningful manner.

In addition, based on the technical concepts described heretofore, a system which calculates design specifications of a medical apparatus which performs a prescribed medical operation on an object region using a high-energy substance as a power source can also be devised. In this case, the devised invention is a system which calculates design specifications of a medical apparatus which performs a prescribed medical operation on an object region using a high-energy substance as a power source, the system including: an apparatus specification unit which specifies the medical apparatus to be an object of calculation of the design specifications, as an object medical apparatus; a first acquisition unit which acquires operation information related to the prescribed medical operation to be performed in the object medical apparatus; a second acquisition unit which acquires region information related to a prescribed object region in which the prescribed medical operation is to be performed; a third acquisition unit which acquires change information related to a change in the prescribed object region, the change being anticipated to occur in the prescribed object region when the prescribed medical operation is performed by the object medical apparatus; and a calculation unit which calculates, based on the operation information acquired by the first acquisition unit, the region information acquired by the second acquisition unit, and the change information acquired by the third acquisition unit, design specification information related to a configuration of the object medical apparatus including energy information related to the high-energy substance to be used for the prescribed medical operation. The operation information, the region information, and the change information in the system which calculates design specifications of the medical apparatus respectively correspond to the substance information, the region information, and the distribution information in the administration apparatus design system described heretofore. Therefore, the medical apparatus design system described above may naturally occur to a person skilled in the art in accordance with the disclosure described heretofore. In a similar manner, a medical apparatus design method and a medical apparatus design program may occur to a person skilled in the art in accordance with the disclosure described heretofore.

In an administration apparatus which administers an administration object substance to an object region using a high-energy substance as a driving source, design specification information related to a configuration of the administration apparatus including energy information related to the high-energy substance can be calculated and convenience of the administration apparatus can be improved.

DETAILED DESCRIPTION OF EMBODIMENTS

While an administration apparatus design system according to an embodiment of the described technology will be hereinafter described with reference to the drawings, before giving a detailed description thereof, a structure and characteristics of an administration apparatus of which design is supported by the system will be described. The administration apparatus is a needle-free administration apparatus which injects a dosing liquid to an object region using combustion energy of high-energy substances including gunpowders and explosives (hereinafter, also simply referred to as "gunpowder"). In other words, the administration apparatus is an apparatus which administers a dosing liquid to an object region without involving an introduction unit which is a physical structure between an apparatus side and the object region. Hereinafter, the administration apparatus 1 will be described.

As described below, the administration apparatus 1 is an apparatus which administers a dosing liquid to an object region, and an administration operation of the dosing liquid corresponds to the administration operation of the administration apparatus. Therefore, the dosing liquid corresponds to the dosing liquid according to the present embodiment. It is to be understood that configurations of the embodiments described below are illustrative and that the described technology is not limited to the configurations of the embodiments described below. Moreover, in the present embodiment, a "distal end side" and a "proximal end side" will be used as terms representing a relative positional relationship in a longitudinal direction of the administration apparatus 1. The "distal end side" represents a position near to a distal end of the administration apparatus 1 to be described later or, in other words, a position near to an injection port 31a, and the "proximal end side" represents a direction opposite to the "distal end side" in the longitudinal direction of the administration apparatus 1 or, in other words, a direction of a side of a drive unit 7.

<Configuration of Administration Apparatus 1>

Figure 1:
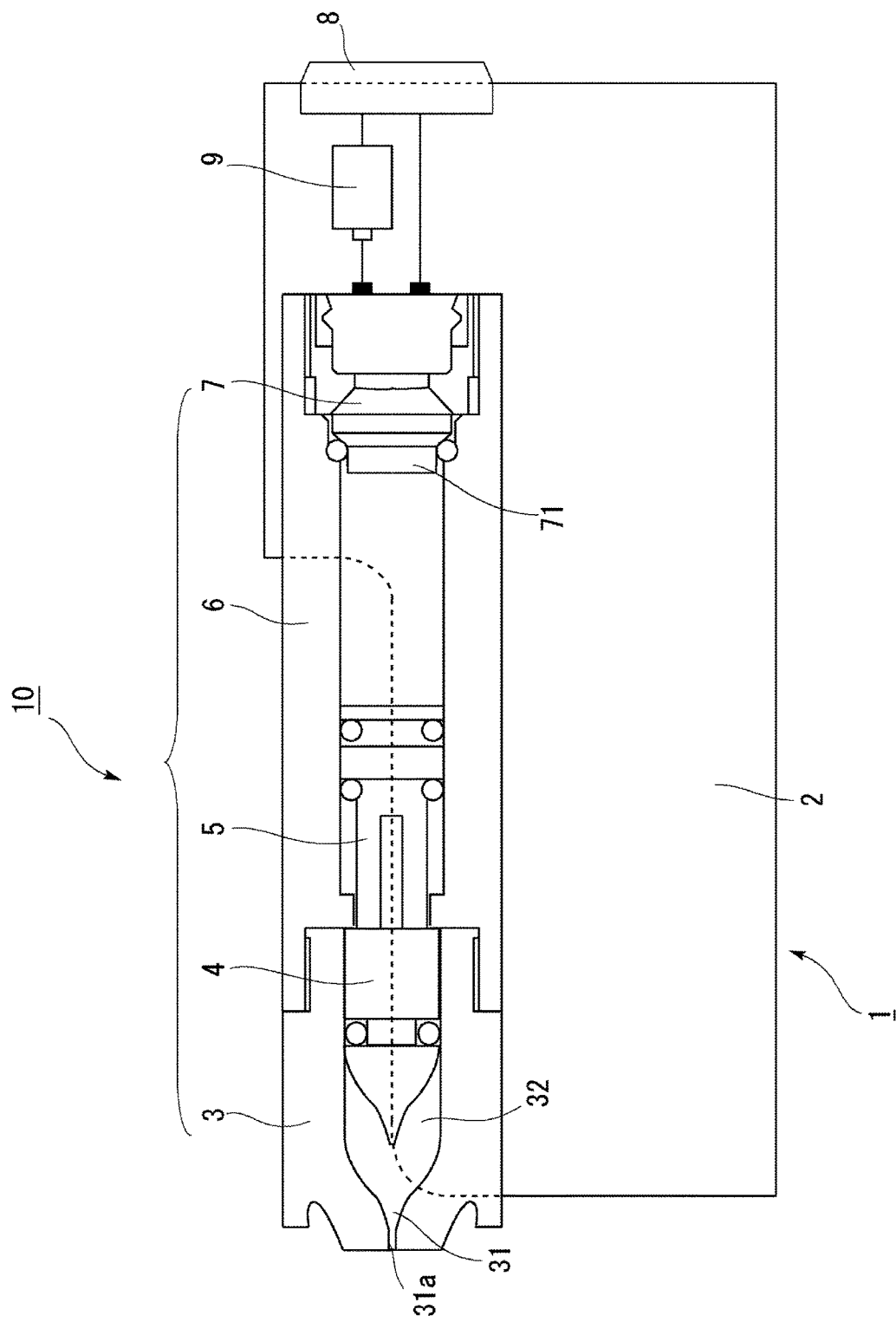
FIG. 1 is a diagram showing a schematic configuration of an administration apparatus driven by gunpowder.

FIG. 1 is a diagram showing a schematic configuration of the administration apparatus 1 and is also a sectional view along a longitudinal direction of the administration apparatus 1. The administration apparatus 1 is constructed by mounting, to a housing 2, an apparatus assembly 10 in which a sub-assembly (refer to FIG. 2A to be described later) 10A which is constituted by a syringe section 3 and a plunger 4 to be described later and a sub-assembly (refer to FIG. 2B to be described later) 10B which is constituted by an administration apparatus main body 6, a piston 5, and the drive unit 7 are integrally assembled. In the following description of the present application, a dosing liquid that is administered to an object region by the administration apparatus 1 is formed by having a liquid medium contain a prescribed substance which exhibits expected efficacy or a function in the object region. In the dosing liquid, the prescribed substance may be in a state of being dissolved in a liquid that is the medium or in a state of being simply mixed without being dissolved.

Examples of the prescribed substance contained in the dosing liquid include biologically-derived substances which can be administered in the object region and substances which produce desired physiological activity, examples of the biologically-derived substances include DNA, RNA, nucleic acids, antibodies, cells, and examples of the physiologically active substances include low molecular medicine, inorganic material such as metal particles for hyperthermia and radiotherapy, and substances and the like having various pharmacological and therapeutic effects including carriers. In addition, the liquid that is the medium of the dosing liquid need only be a substance preferable for administering the prescribed substances into the object region and may be either water-based or oil-based. Furthermore, as long as the prescribed substance can be administered with the administration apparatus 1, a viscosity of the liquid that is the medium is also not particularly limited. In addition, the object region that is an administration object of the dosing liquid is a region to which the prescribed substance is to be administered, and examples of the object region include cells or tissue (skin or the like), an organ or system (an eye, the heart, a liver, or the like), and the like of a living organism. Moreover, a component of a living organism can be set as the object region in a state where the component is separated from a main body of the living organism as long as such separation does not pose any problems. In other words, both ex-vivo administration of the prescribed substance to an object region (tissue or an organ) and in-vitro administration of the prescribed substance to an object region (cultured cells or cultured tissue) are also included in the scope of the administration apparatus according to the present embodiment.

As described above, the apparatus assembly 10 is configured to be detachable from and attachable to the housing 2. A filling chamber 32 (refer to FIG. 2A) formed between the syringe section 3 and the plunger 4 included in the apparatus assembly 10 is filled with the dosing liquid, and the apparatus assembly 10 is a unit which is replaced every time an injection of the dosing liquid is performed. On the other hand, a battery 9 that supplies power to an igniter 71 included in the drive unit 7 of the apparatus assembly 10 is included on a side of the housing 2. Power supply from the battery 9 is performed via a wiring between an electrode on the side of the housing 2 and an electrode on a side of the drive unit 7 of the apparatus assembly 10 when a user performs an operation that involves pressing down a button 8 provided on the housing 2. Moreover, shapes and positions of the electrode on the side of the housing 2 and the electrode on the side of the drive unit 7 of the apparatus assembly 10 are designed so that the electrodes automatically come into contact with each other when the apparatus assembly 10 is mounted to the housing 2. In addition, the housing 2 is a unit which can be repetitively used as long as power that can be supplied to the drive unit 7 remains in the battery 9. Furthermore, in the housing 2, when power of the battery 9 is used up, only the battery 9 may be replaced and the housing 2 may be continuously used.

Configurations of the sub-assemblies 10A and 10B and detailed configurations of the syringe section 3, the plunger 4, the piston 5, the administration apparatus main body 6, and the drive unit 7 which are included in both subassemblies will now be described with reference to FIGS. 2A and 2B. The syringe section 3 has a nozzle section 31 which includes the filling chamber 32 that is a space capable of storing the dosing liquid and, at the same time, the plunger 4 is arranged in the sub-assembly 10A so as to be slidable in the filling chamber 32.

As a body 30 of the syringe section 3, for example, known nylon 6-12, polyallylate, polybutylene terephthalate, polyphenylene sulfide, a liquid crystal polymer, or the like can be used. In addition, these resins may contain a filler such as glass fiber or a glass filler, in which case polybutylene terephthalate can contain 20% by mass to 80% by mass of glass fiber, polyphenylene sulfide can contain 20% by mass to 80% by mass of glass fiber, and a liquid crystal polymer can contain 20% by mass to 80% by mass of minerals.

In addition, in the filling chamber 32 formed inside the body 30, the plunger 4 is arranged so as to be slidable in a direction of the nozzle section 31 (a distal end-side direction), and a space formed between the plunger 4 and the body of the syringe section 3 is a space in which a dosing liquid 320 is to be stored. As the plunger 4 slides inside the filling chamber 32, the dosing liquid 320 stored in the filling chamber 32 is pressed and injected from the injection port 31a provided on a distal end side of the nozzle section 31. To this end, the plunger 4 is formed of a material which enables the plunger 4 to slide smoothly in the filling chamber 32 and which prevents the dosing liquid 320 from leaking out from the side of the plunger 4. Specific examples of a material of the plunger 4 include butyl rubber and silicone rubber. Further examples include a styrene-based elastomer, a hydrogenated styrene-based elastomer, and a styrene-based elastomer or a hydrogenated styrene-based elastomer mixed with a polyolefin such as polyethylene, polypropylene, polybutene, or alpha-olefin copolymer, an oil such as liquid paraffin or processing oil, or a powdered inorganic substance such as talc, cast, or mica. In addition, a polyvinyl chloride-based elastomer, an olefin-based elastomer, a polyester-based elastomer, a polyamide-based elastomer, a polyurethane-based elastomer, various rubber materials (in particular, vulcanized rubber materials) such as natural rubber, isoprene rubber, chloroprene rubber, nitrile-butadiene rubber, styrene-butadiene rubber, and mixtures thereof can also be adopted as the material of the plunger 4. Furthermore, for the purpose of securing or adjusting slidability between the plunger 4 and the syringe section 3, a surface of the plunger 4 or a surface of the filling chamber 32 of the syringe section 3 may be coated or surface-treated using various substances. As the coating agent, PTFE (polytetrafluoroethylene), silicone oil, diamond-like carbon, nanodiamond, and the like can be used, and an injection pressure transition and vibration elements thereof to be described later may be controlled by using these material to adjust slidability to a desired range.

Figure 2A:
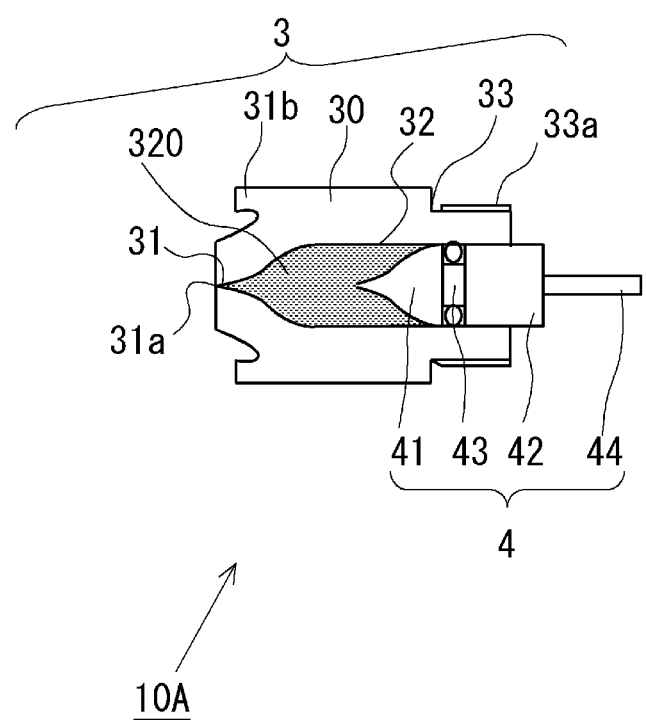
FIG. 2A is a diagram showing a schematic configuration of a first sub-assembly constituting an apparatus assembly to be built into the administration apparatus shown in FIG. 1.

As shown in FIG. 2A, the plunger 4 has a head section 41 and a barrel section 42, and the head section 41 and the barrel section 42 are connected by a neck section 43 with a diameter that is smaller than diameters of the head section 41 and the barrel section 42. The diameter of the neck section 43 is made small in this manner in order to form a storage space of an O ring that constitutes a seal member. Moreover, a contour on a distal end side of the head section 41 has a shape that more or less conforms to a contour of an inner wall surface of the nozzle section 31. Accordingly, when the plunger 4 slides to the side of the nozzle section 31 during injection of the dosing liquid and reaches a deepest position that is an innermost position in the filling chamber 32, a gap formed between the plunger 4 and the inner wall surface of the nozzle section 31 can be made as small as possible and the dosing liquid 320 can be prevented from remaining inside the filling chamber 32 and becoming waste. However, the shape of the plunger 4 is not limited to any particular shape as long as a desired effect can be obtained with the administration apparatus according to the present embodiment. In addition, an injection pressure transition and vibration elements thereof to be described later can be controlled by providing a single protrusion or a plurality of protrusions in the barrel section 42 and adjusting a contact area between the plunger 4 and the filling chamber 32 or varying a shape of the protrusions in order to adjust the slidability between the plunger 4 and the syringe section 3.

Furthermore, the plunger 4 is provided with a rod section 44 which extends further in a direction of the proximal end side from an end surface on the proximal end side of the barrel section 42. While a diameter of the rod section 44 is sufficiently smaller than that of the barrel section 42, the diameter is large enough to enable the user to grip the rod section 44 and move the rod section 44 inside the filling chamber 32. In addition, a length of the rod section 44 is determined so that the rod section 44 protrudes from the end surface on the proximal end side of the syringe section 3 and the user can grip the rod section 44 even when the plunger 4 is at the deepest position of the filling chamber 32 of the syringe section 3.

Let us now return to the description of the syringe section 3. An inner diameter of a flow path provided in the nozzle section 31 on the side of the syringe section 3 is formed narrower than an inner diameter of the filling chamber 32. According to such a configuration, the dosing liquid 320 having been pressurized to high pressure is injected to the outside from the injection port 31a of the flow path. In consideration thereof, a vicinity of the nozzle section 31 on a distal end side of the syringe section 3 is provided with an annular shield section 31b so as to surround a periphery of the injection port 31a. For example, when the dosing liquid is to be injected by pressing the injection port 31a against a superficial layer of an administration object region such as human skin, the injected dosing liquid can be shielded by the shield section 31b and prevented from spattering around the injection port 31a. Moreover, a certain amount of yielding of the skin when the injection port is pressed against the skin increases contactability between the injection port and the skin and can suppress scattering of the dosing liquid. In consideration thereof, as shown in FIG. 2A, a distal end of the nozzle section 31 where the injection port 31a is positioned may slightly protrude in an injection direction of the dosing liquid from the end surface of the shield section 31b.

In addition, in the neck section 33 that is positioned on the proximal end side of the syringe section 3, a screw section 33a for coupling the administration apparatus main body 6 on the side of the sub-assembly 10B to be described later and the syringe section 3 to each other is formed. A diameter of the neck section 33 is set smaller than the diameter of the body 30.

Next, the sub-assembly 10B that includes the piston 5, the administration apparatus main body 6, and the drive unit 7 will be described with reference to FIG. 2B. The piston 5 is configured to be pressurized by a combustion product generated by the igniter 71 of the drive unit 7 and to slide inside a through-hole 64 formed inside a body 60 of the administration apparatus main body 6. In the administration apparatus main body 6, a coupling depression 61 is formed on a distal end side with the through-hole 64 as a reference. The coupling depression 61 is a portion which is coupled with the neck section 33 of the syringe section 3 described above, and a screw section 62a which screws with the screw section 33a provided in the neck section 33 is formed on a side wall surface 62 of the coupling depression 61. In addition, while the through-hole 64 and the coupling depression 61 are connected by a communicating section 63, a diameter of the communicating section 63 is set smaller than a diameter of the through-hole 64. Furthermore, in the administration apparatus main body 6, a drive unit depression 65 is formed on a proximal end side with the through-hole 64 as a reference. The drive unit 7 is to be arranged in the drive unit depression 65.

In addition, the piston 5 is made of metal and has a first barrel section 51 and a second barrel section 52. The piston 5 is arranged inside the through-hole 64 so that the first barrel section 51 faces a side of the coupling depression 61 and, at the same time, the second barrel section 52 faces aside of the drive unit depression 65. The piston 5 slides inside the through-hole 64 of the administration apparatus main body 6 while the first barrel section 51 and the second barrel section 52 oppose an inner wall surface of the through-hole 64. Moreover, the first barrel section 51 and the second barrel section 52 are connected by a coupling section that is narrower than diameters of the respective barrel sections, and an O ring or the like is arranged in a space between the barrel sections which is formed as a result of the barrel sections being connected by the coupling section in order to enhance adhesiveness with the inner wall surface of the through-hole 64. In addition, the piston 5 may be made of resin, in which case metal may be used in combination with the resin in portions that require heat resistance or pressure resistance.

An end surface on a distal end side of the first barrel section 51 is provided with a pressing column section 53 of which a diameter is smaller than the first barrel section 51 and also smaller than the diameter of the communicating section 63 of the administration apparatus main body 6. The pressing column section 53 is provided with a storage hole 54 which opens on an end surface on a distal end side of the pressing column section 53, of which a diameter is equal to or larger than the diameter of the rod section 44, and of which a depth is greater than the length of the rod section 44. As a result, when the piston 5 is pressurized by a combustion product of the igniter 71, the pressing column section 53 can transfer the combustion energy of the combustion product to the end surface on the proximal end side of the barrel section 42 of the plunger 4 via the end surface on the distal end side of the pressing column section 53. Moreover, a shape of the piston 5 is similarly not limited to the shape illustrated in FIG. 2B.

Next, the drive unit 7 will be described. The drive unit 7 has a body 72 thereof formed in a cylindrical shape and has, inside the drive unit 7, the igniter 71 which is an electric igniter that burns an ignition charge to generate energy for injection, and the drive unit 7 is arranged in the drive unit depression 65 as described above so as to be capable of transferring combustion energy by the igniter 71 to the second barrel section 52 of the piston 5. Specifically, the body 72 of the drive unit 7 may be constructed by fixing an injection-molded resin to a metal collar. Known methods can be used to perform the injection molding. A resin material of the body 72 of the drive unit 7 is the same resin material used to form the body 30 of the syringe section 3.

The ignition charge used in the igniter 71 corresponds to the so-called high-energy substance. In addition, the combustion energy of the ignition charge becomes the administration energy for administering the dosing liquid to the object region by the administration apparatus 1. Favorable examples of the ignition charge include gunpowder (ZPP) containing zirconium and potassium perchlorate, gunpowder (THPP) containing titanium hydride and potassium perchlorate, gunpowder (TiPP) containing titanium and potassium perchlorate, gunpowder (APP) containing aluminum and potassium perchlorate, gunpowder (ABO) containing aluminum and bismuth oxide, gunpowder (AMO) containing aluminum and molybdenum oxide, gunpowder (ACO) containing aluminum and copper oxide, and gunpowder (AFO) containing aluminum and iron oxide, and gunpowder consisting of a combination of a plurality of these gunpowders. These gunpowders exhibit characteristics in that, while high-temperature and high-pressure plasma is generated during combustion immediately after ignition, generated pressure drops abruptly once a combustion product reaches normal temperature and condenses since the combustion product does not have a gaseous component. Gunpowders other than the above may be used as the ignition charge insofar as appropriate administration can be performed.

In addition, although a gas generating agent is not particularly arranged inside the administration apparatus main body 6 shown in FIG. 1 as an additional gunpowder component, in order to adjust a pressure transition applied to the dosing liquid via the piston 5, a gas generating agent or the like which is burned by the combustion product created by powder combustion in the igniter 71 to generate gas can also be arranged inside the administration apparatus main body 6. An arrangement location of the gas generating agent is a location where the gas generating agent may be exposed to the combustion product from the igniter 71 such as a location depicted by a dotted line in FIG. 2B. The gas generating agent to be arranged inside the igniter 71 is already well known as disclosed in WO 2001/031282 and Japanese Patent Application Laid-open No. 2003-25950. In addition, examples of the gas generating agent include a single-base smokeless powder consisting of 98% by mass of nitrocellulose, 0.8% by mass of diphenylamine, and 1.2% by mass of potassium sulfate. Furthermore, various gas generating agents used in an airbag gas generator or a seat-belt pretensioner gas generator can also be used. By adjusting dimensions or a size, a shape, and particularly a surface profile of a gas generating agent when arranging the gas generating agent inside the through-hole 64, a combustion completion time of the gas generating agent can be varied and, accordingly, a pressure transition applied to the dosing liquid can be adjusted and a desired injection pressure transition of the dosing liquid can be achieved. In the present embodiment, the gas generating agent used when necessary is also included in the drive unit 7.

Moreover, filling of the dosing liquid 320 in the sub-assembly 10A is performed in a state where the plunger 4 has been inserted to the deepest position by immersing the injection port 31a into a container filled with the dosing liquid and drawing back the plunger 4 to an opening side of the filling chamber 32 or, in other words, the proximal end side of the syringe section 3 while maintaining this state. At this point, the plunger 4 has been drawn out until an end surface on the proximal end side of the barrel section 42 of the plunger 4 reaches a position slightly protruding from the end surface on the proximal end side of the syringe section 3.

Figure 2B:
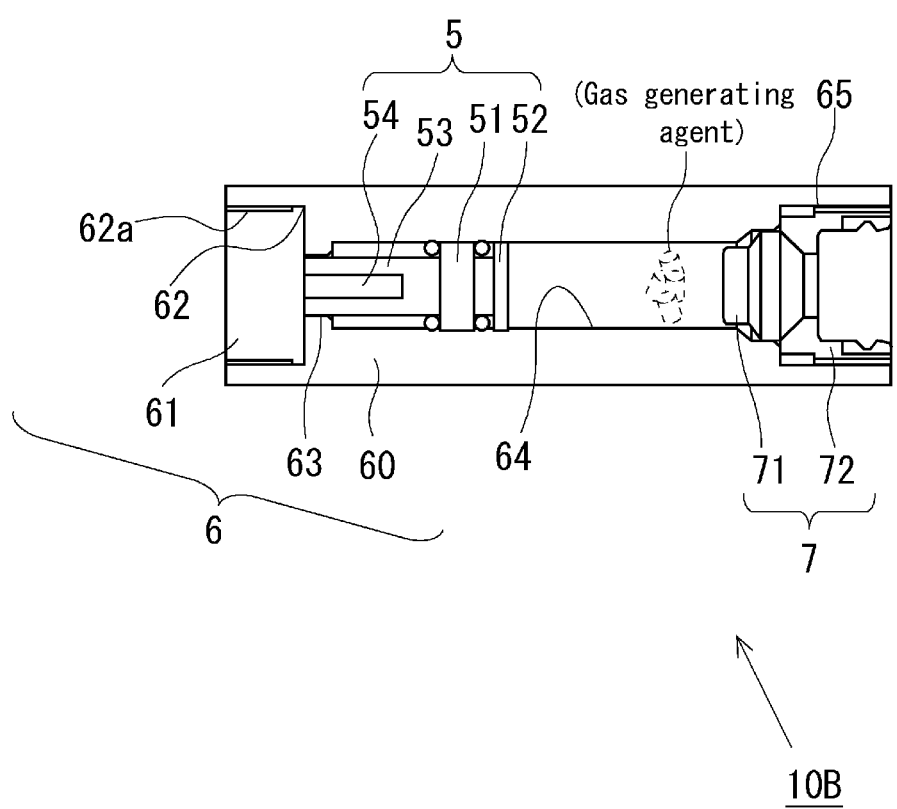
FIG. 2B is a diagram showing a schematic configuration of a second sub-assembly constituting an apparatus assembly to be built into the administration apparatus shown in FIG. 1.

In addition, in the sub-assembly 10B, the piston 5 is first inserted from the proximal end side of the administration apparatus main body 6 shown in FIG. 2B. In doing so, the piston 5 is inserted into the through-hole 64 so that the pressing column section 53 faces the side of the coupling depression 61. Furthermore, the piston 5 is positioned so that an end surface on the distal end side of the piston 5 or, in other words, an end surface on the distal end side of the pressing column section 53 on which the storage hole 54 opens protrudes by a prescribed amount from a bottom surface of the coupling depression 61 (a surface perpendicular to the side wall surface 62). The piston 5 may be positioned by appropriately using known techniques such as marking a symbol for positioning inside the through-hole 64 and using a positioning jig. Subsequently, the drive unit 7 is mounted to the drive unit depression 65. Moreover, a fixing force of the piston 5 in the through-hole 64 is set depending on pressure received by the drive unit 7 from a combustion product by the igniter 71 to a level which enables the piston 5 to slide inside the through-hole 64 in a sufficiently smooth manner and, at the same time, a level which sufficiently counteracts a force received by the piston 5 from the plunger 4 when the sub-assembly 10A is mounted to the sub-assembly 10B and which prevents the position of the piston 5 from fluctuating.

The sub-assembly 10A configured in this manner is mounted to the sub-assembly 10B by screwing of the screw sections 33a and 62a to form the apparatus assembly 10. At this point, as coupling of both sub-assemblies advances, the rod section 44 of the plunger 4 enters the storage hole 54 provided in the pressing column section 53 of the piston 5 and becomes stored in the storage hole 54 and, finally, the end surface on the distal end side of the pressing column section 53 comes into contact with the end surface on the proximal end side of the barrel section 42 of the plunger 4. Moreover, since the storage hole 54 is large enough to store the rod section 44, in this contact state, an inner wall surface at the back of the storage hole 54 (in particular, a bottom surface of the storage hole 54) is not in contact with the end section on the proximal end side of the rod section 44 and, therefore, the rod section 44 is not subjected to a load from the side of the piston 5. Furthermore, once the coupling advances to a final screwing position, since a position of the piston 5 is fixed to the through-hole 64 with a sufficient friction force, the plunger 4 is pushed by the pressing column section 53 so as to advance toward the side of the injection port 31a and the plunger 4 is positioned inside the syringe section 3. Moreover, a part of the dosing liquid 320 corresponding to the amount by which the plunger 4 is pushed is discharged from the injection port 31a.

The formation of the apparatus assembly 10 is completed once the plunger 4 is positioned at a final position in this manner. In the apparatus assembly 10, the piston 5 is in a state of being positioned at a prescribed position with respect to the administration apparatus main body 6, and a position of the plunger 4 in the filling chamber 32 of the syringe section 3 is finally mechanically determined with the piston 5 as a reference. Since the final position of the plunger 4 is a position that is uniquely determined in the apparatus assembly 10, an amount of the dosing liquid 320 to be finally stored in the filling chamber 32 can be adjusted to a prescribed amount determined in advance.

Subsequently, the apparatus assembly 10 is mounted to the housing 2, and when the button 8 is pressed by the user in a state where the injection port 31a is in contact with the object region, the dosing liquid 320 is pressurized via the piston 5 and the plunger 4, injection of the dosing liquid 320 is executed, and the dosing liquid 320 is administered into the object region.

<Injection Control of Dosing Liquid>

Figure 3:
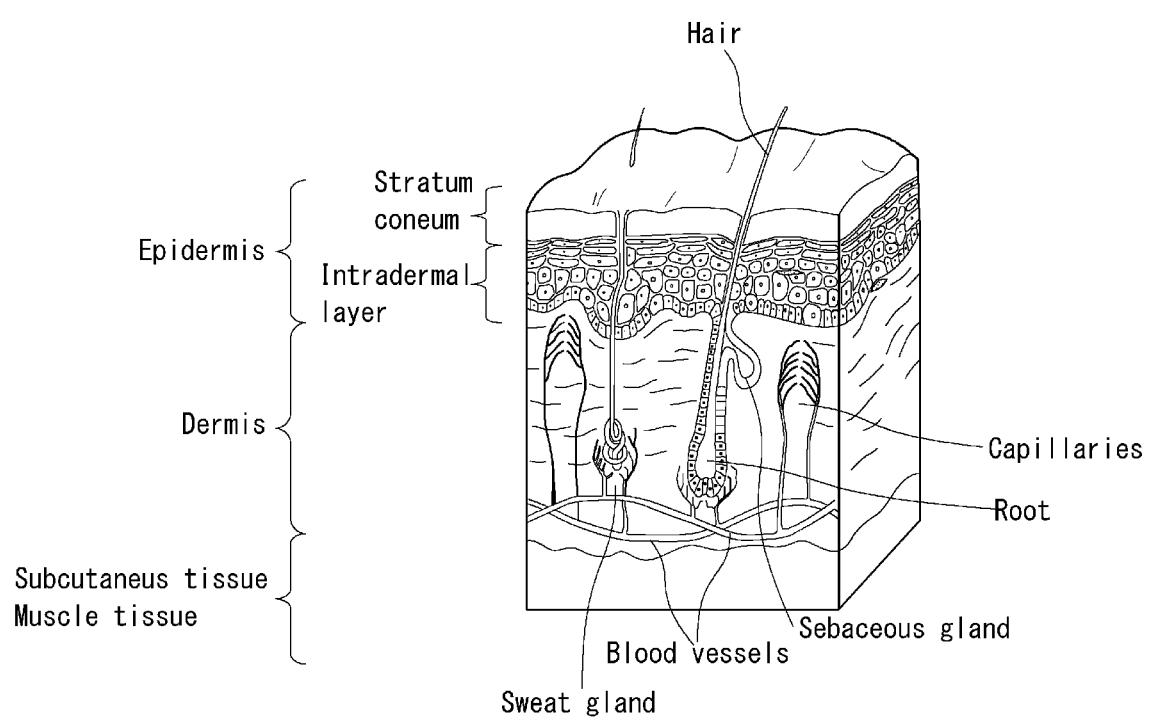
FIG. 3 is a diagram illustrating a skin structure that is an object region of administration.

Examples of the object region of the administration apparatus 1 include a skin structure of a living organism such as a human or livestock. FIG. 3 schematically shows an anatomical structure of human skin. The human skin is structured in layers in the depth direction from the skin surface side by the epidermis, the dermis, and subcutaneous tissue and muscle tissue, and the epidermis can be further divided into the layers of the stratum corneum and the intradermal layer. The respective layers of the skin structure differ from each other in cells and the like which mainly make up tissue of the layer and in tissue characteristics.

Specifically, the stratum corneum is mainly made up of keratinocytes and functions as a so-called barrier layer due to its position on an outermost side of skin. Generally, a thickness of the stratum corneum is around 0.01 to 0.015 mm and the keratinocytes provide surface protection for a human. Therefore, the stratum corneum is required to be relatively strong in order to physically cut off the inside of a human body from the external environment. In addition, the intradermal layer is made up of dendritic cells (Langerhans cells) and pigment cells (melanocytes), the epidermis is made up of the stratum corneum and the intradermal layer, and a thickness of the epidermis is generally around 0.1 to 2 mm. The dendritic cells in the intradermal layer are thought to be cells involved in antigen-antibody reactions. This is because ingesting an antigen makes the dendritic cells aware of the presence of the antigen and an antigen-antibody reaction which activates lymphocytes that attack foreign objects is more readily induced. On the other hand, pigment cells in the intradermal layer have a function of preventing the effect of ultraviolet rays irradiated from the external environment. In addition, the dermis is lined with cutaneous blood vessels and capillaries that form a complex pattern, and sweat glands for regulating body temperature, roots of body hair (including head hair) and sebaceous glands that accompany roots are also present in the dermis. Furthermore, the dermis is a layer that communicates between the inside of the human body (subcutaneous tissue, muscular tissue) and the epidermis, and is constructed so as to contain fibroblasts and collagen cells. Therefore, a state of the dermis plays a major role in the occurrence of so-called wrinkles, hair loss, and the like due to a shortage of collagen and elastin.

As described above, the skin structure of a human is generally formed in layers and unique anatomical functions are exhibited by cells, tissue, and the like which primarily make up each layer. This means that, when using medical treatment or the like on skin, a substance for the treatment is desirably administered to a location (depth) of the skin structure corresponding to a therapeutic purpose of the medical treatment. For example, since dendritic cells are present in the intradermal layer, a more effective antigen-antibody reaction can be expected by administering a vaccine to the intradermal layer. In addition, since pigment cells are present in the intradermal layer, even when performing a beauty treatment for so-called skin whitening, prescribed substances for skin whitening are required to be administered to the intradermal layer. Furthermore, since fibroblasts and collagen cells are present in the dermis, an effective beauty treatment effect is expected when injecting proteins, enzymes, vitamins, amino acids, minerals, sugars, nucleic acids, and various growth factors (epithelial cells and fibroblasts) for removing wrinkles of the skin. Moreover, it is said that a favorable hair regrowth treatment involves stem cell infusion in which hair papilla cells, epidermal stem cells, and the like are autologously cultured and autologously transplanted into the scalp or injecting several types of growth factors and nutritional components extracted from stem cells into a vicinity of the dermis.

As described above, while a prescribed substance administered according to a therapeutic purpose and a position (depth) in the skin structure at which the prescribed substance is desirably administered individually correspond to each other, it is not easy to deliver the substance to a targeted arrival position. In addition, even when the prescribed substance is able to reach the target arrival position, a sufficient desired effect by the prescribed substance cannot be expected if cells in the vicinity of the arrival position end up being destroyed by a dosing liquid including the prescribed substance. Furthermore, if the dosing liquid had applied some kind of load to tissue and cells through which the dosing liquid had passed in the process of reaching the arrival position and has destroyed the tissue or cells, such destruction is to be recognized by the user as an internal hemorrhage, pain, and the like and therefore impart a feeling of discomfort to the user. In particular, when no structure (introduction unit) which guides the dosing liquid to the inside of an object region is present between an apparatus to administer the dosing liquid such as the administration apparatus 1 and the object region, a constant amount of energy (in the case of the present embodiment, this energy is combustion energy by the igniter 71) is to be imparted to the dosing liquid to enable the dosing liquid to penetrate to the inside of the object region. Since the dosing liquid is imparted with relatively high energy and injected toward the object region to enable the dosing liquid to penetrate into the object region, an unnecessary dynamic action is likely to be performed on components (for example, cells) of the object region and invasiveness to the object region cannot be necessarily described as being low. In addition, in conventional art, injections of a dosing liquid which sufficiently take such invasiveness to the object region into consideration are not carried out and, consequently, efficacy and the like due to the prescribed substance are not sufficiently elicited.

In consideration thereof, in the present embodiment, for example, minimal invasiveness to an object region is defined as administering a dosing liquid so that functions of organs, tissue, and the like of a living organism are not damaged during administration or administering the dosing liquid so that damage to such functions are minimized. Alternatively, when cells of a living organism are used as an object region, minimal invasiveness to an object region is defined as administering a dosing liquid so as not to cause unnecessary cell death or administering the dosing liquid so as to minimize unnecessary cell death. Based on the above, the administration apparatus 1 according to the present embodiment adopts a configuration in which pressurization of a dosing liquid by combustion energy generated by the drive unit 7 is adjusted so that a pressure transition of the dosing liquid injected from the administration apparatus 1 exhibits minimal invasiveness with respect to an object region. Details thereof will be described below.

Figure 4A:
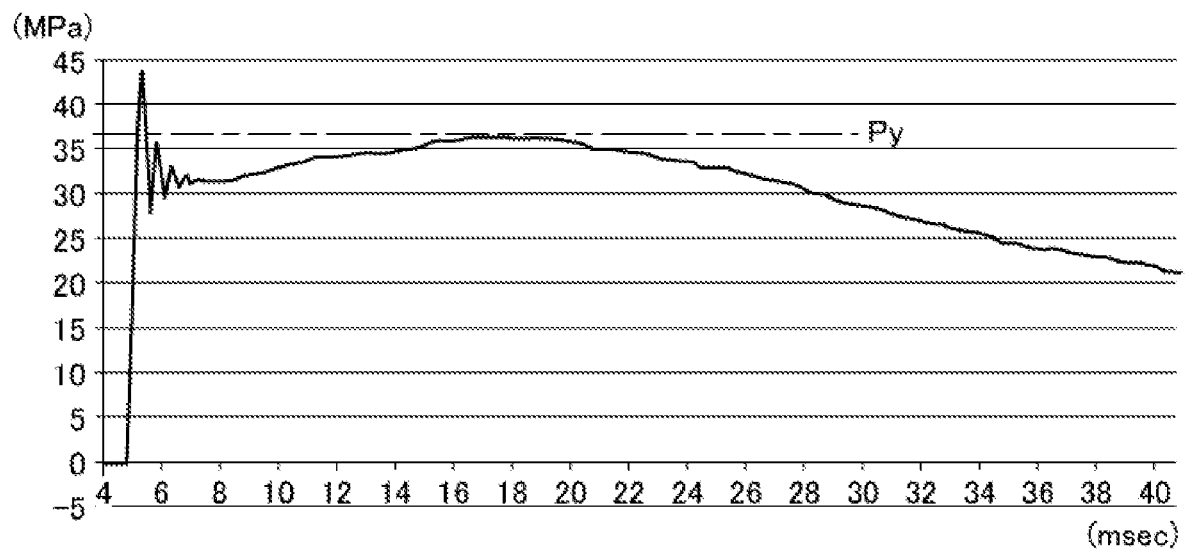
FIG. 4A and FIG. 4B are a diagram showing an injection pressure transition of a dosing liquid injected by the administration apparatus shown in FIG. 1.
Figure 4B:
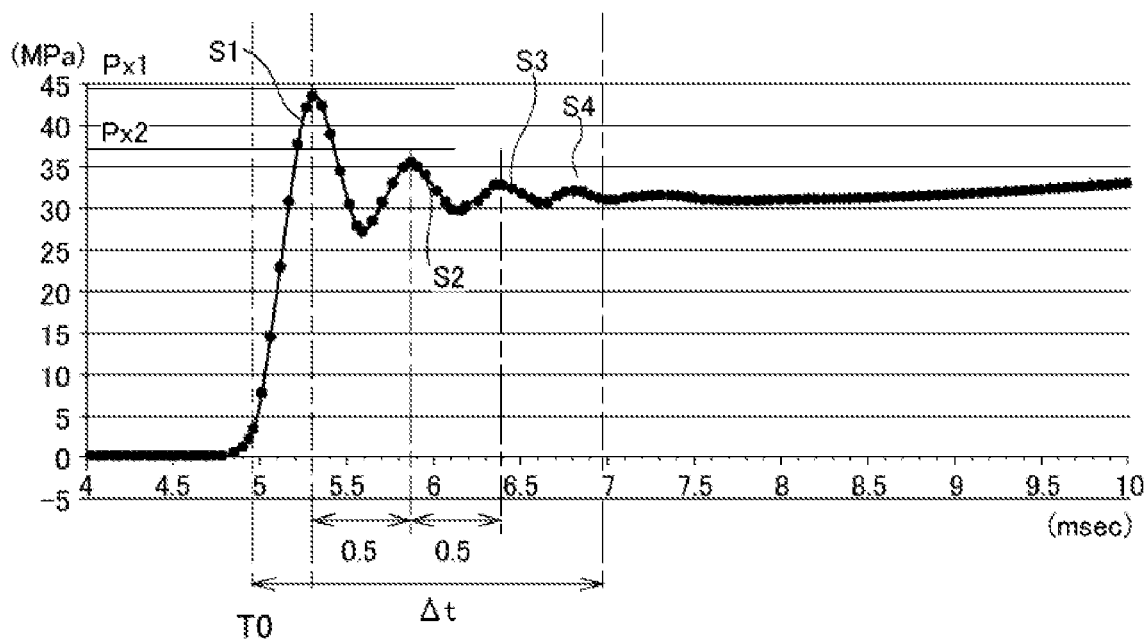

FIG. 4A and FIG. 4B are a diagram showing a transition of pressure (hereinafter, simply referred to as "injection pressure") of a dosing liquid injected from the injection port 31a when the dosing liquid is injected by driving of the drive unit 7 in the administration apparatus 1. In FIG. 4A and FIG. 4B, an abscissa represents elapsed time in milliseconds and an ordinate represents injection pressure in MPa. Moreover, injection pressure can be measured using conventional art. For example, in a similar manner to a measurement method described in Japanese Patent Application Laid-open No. 2005-21640, an injection force can be measured by a method involving applying force of an injection in a distributed manner to a diaphragm of a load cell arranged on a downstream side of a nozzle, sampling output from the load cell with a data sampling apparatus via a detection amplifier, and storing the sampled output as an injection force (N) per unit time. Injection pressure is calculated by dividing an injection force measured in this manner by an area of the injection port 31a of the administration apparatus 1. The example shown in FIG. 4A and FIG. 4B represents a transition of injection pressure obtained by adopting ZPP (containing zirconium and potassium perchlorate) as an ignition charge of the igniter 71 inside the drive unit 7 and, at the same time, arranging a gas generating agent inside the through-hole 64.

FIG. 4A represents a transition of injection pressure during a period of approximately 40 milliseconds from start of combustion with a time point at which the button 8 is pressed in the drive unit 7 as an origin, and FIG. 4B displays an enlargement of an injection pressure transition in an initial period (approximately 10 milliseconds from the origin) in the pressure transition shown in FIG. 4A. Moreover, rising of injection pressure occurs not at the origin but in a vicinity of 5 milliseconds because a certain amount of time is required for the ignition charge to burn, the dosing liquid to be pressurized as the piston 5 is propelled by the combustion energy of the ignition charge, and the dosing liquid to be injected from the injection port 31a. As is apparent from FIG. 4A and FIG. 4B, in the injection pressure transition, a plurality of pressure vibration elements S1 to S4 are present in a prescribed period of time Δt from the rise timing T0 to approximately 2 milliseconds thereafter, and pressure vibration generally converges once the prescribed period of time Δt elapses. Moreover, in the present embodiment, one cycle in which injection pressure rises and drops in pressure vibration is to be handled as one pressure vibration element.

More specifically, in the prescribed period of time Δt from the rise timing T0, a pressure vibration element S1 (hereinafter, referred to as a "first vibration element S1") is initially generated. The first vibration element S1 is an injection pressure transition of a period after a peak value Px1 (approximately 45 MPa) once arrives from injection pressure (approximately 0 MPa) at the rise timing T0 and before a next local minimum value arrives. In addition, a variation width (peak to peak) of the injection pressure in the period is defined as a total amplitude of the first vibration element S1 and, specifically, the total amplitude of the first vibration element S1 is approximately 45 MPa. The first vibration element S1 is further followed by a second vibration element S2, a third vibration element S3, and a fourth vibration element S4. The second vibration element S2 is an injection pressure transition of a period after a peak value Px2 (approximately 37 MPa) arrives from a timing of the end of the first vibration element S1 and before a next local minimum value arrives. In addition, a variation width (peak to peak) of the injection pressure in the period is defined as a total amplitude of the second vibration element S2 and, specifically, the total amplitude of the second vibration element S2 is approximately 10 MPa. With respect to the third vibration element S3 and the fourth vibration element S4, a period that defines each vibration element and a total amplitude of each vibration element are similar to those of the second vibration element S2 and, although a detailed description thereof will be omitted, the total amplitude of the third vibration element S3 and the total amplitude of the fourth vibration element S4 have decreased with the passage of time. In other words, in the prescribed period of time Δt, the pressure transition becomes a damped vibration with the passage of time, and after the lapse of the prescribed period of time Δt, the pressure transition enters a state where the vibration has more or less converged.

Furthermore, let us focus on a period of the pressure vibration in the prescribed period of time Δt. A period calculated from a peak value of the first vibration element S1 and a peak value of the second vibration element S2 is approximately 0.5 milliseconds, and a period calculated from the peak value of the second vibration element S2 and a peak value of the third vibration element S3 is approximately 0.5 milliseconds. While a period immediately before arrival of a converged state is slightly shorter, it is evident that the transition of injection pressure takes place at a generally constant period in the prescribed period of time Δt. Accordingly, it is shown that the injection pressure transition in the prescribed period of time Δt is a pressure vibration at a frequency of around 2000 Hz.

Moreover, a pressure fluctuation in the prescribed period of time Δt is mainly attributable to combustion of the ignition charge of the igniter 71. In addition, in a vicinity of a timing at which the prescribed period of time Δt lapses, combustion of the gas generating agent inside the through-hole 64 is started by a combustion product of the ignition charge and combustion energy thereof starts to further act on the dosing liquid. As a result, as shown in FIG. 4A, after the lapse of the prescribed period of time Δt, injection pressure increases one again and a peak value Py arrives at a timing of approximately 18 milliseconds. Moreover, subsequently, the injection pressure gradually drops with the passage of time. Since a combustion rate of the gas generating agent is lower than a combustion rate of the ignition charge, a rate of increase of injection pressure due to combustion of the gas generating agent also becomes relatively lower.

How a dosing liquid affects components of an object region and exhibits minimal invasiveness due to injection pressure indicating such transition characteristics will be described using an example of administrating the dosing liquid to the epidermis of the skin structure shown in FIG. 3. Various bonding means are present in basal cells in the stratum basale of the epidermis. The epidermis and the dermis are bonded in close contact by an epidermal basement membrane structure, and a portion where the epidermis and the dermis are in contact with each other is called an epidermal basement membrane. A transparent band is present between a cell membrane and the basal lamina of basal cells, and hemidesmosomes play a major role in the bonding between the basal cells and the basement membrane structure. In addition, desmosomes and gap junctions are involved in the bonding of adjacent basal cells. A desmosome has a portion on an inner side of the cell membrane called an attachment plaque and a structure responsible for bonding between cells through the cell membrane. Furthermore, a gap junction is formed by connexins and is structured so as to bond adjacent cells across a gap of 2 to 3 nm. Due to these bonding means, prevention of separation of the epidermis and the dermis from one another and retention of moisture in the skin structure are achieved.

As described above, in the skin structure of a living organism, cells themselves are enclosed in the cell membrane and, at the same time, various bonding means are present between the cells. Therefore, in order to demonstrate minimal invasiveness to cells and the like when the skin structure is used as an object region of administration of a dosing liquid, control of injection pressure which suitably counteracts a bonding force between cells created by the bonding means while avoiding unnecessary dynamic action to cell membranes is conceivably important. In addition, technical concepts related to such injection pressure are conceivably applicable in a similar manner to object regions in a living organism other than the skin structure.

In the injection pressure transition shown in FIG. 4B, within the prescribed period of time Δt, the first vibration element S1 with highest peak pressure is initially generated, followed by the sequential arrivals of the second, third, and fourth vibration elements S2 to S4. Through this process, the total amplitude of the respective vibration elements gradually decreases and pressure vibration is dampened. Causing injection pressure to vibrate in a damped manner in the prescribed period of time Δt as described above enables the dosing liquid having been imparted with relatively high energy to enable the dosing liquid to penetrate a superficial layer of the object region in an initial stage of administration to exert a dynamic action on cell membrane in a distributed manner and conceivably enables destruction of cell membrane to be avoided. In particular, as described above, it is shown that the injection pressure transition in the prescribed period of time Δt is a pressure vibration at a frequency of around 2000 Hz which is relatively close to a natural frequency of cells of a living organism. Therefore, when a dosing liquid having the injection pressure transition shown in FIG. 4B enters the object region, cells become more susceptible to large vibrations and, as a result, diffusion of the dosing liquid between the cells is conceivably promoted while preventing unnecessary dynamic action from being exerted on cell membrane. From the above, a vibrational frequency of injection pressure during the prescribed period of time Δt is favorably a frequency belonging to a prescribed frequency range associated with a natural frequency of a component (cells or the like) of the object region.

Figure 5:
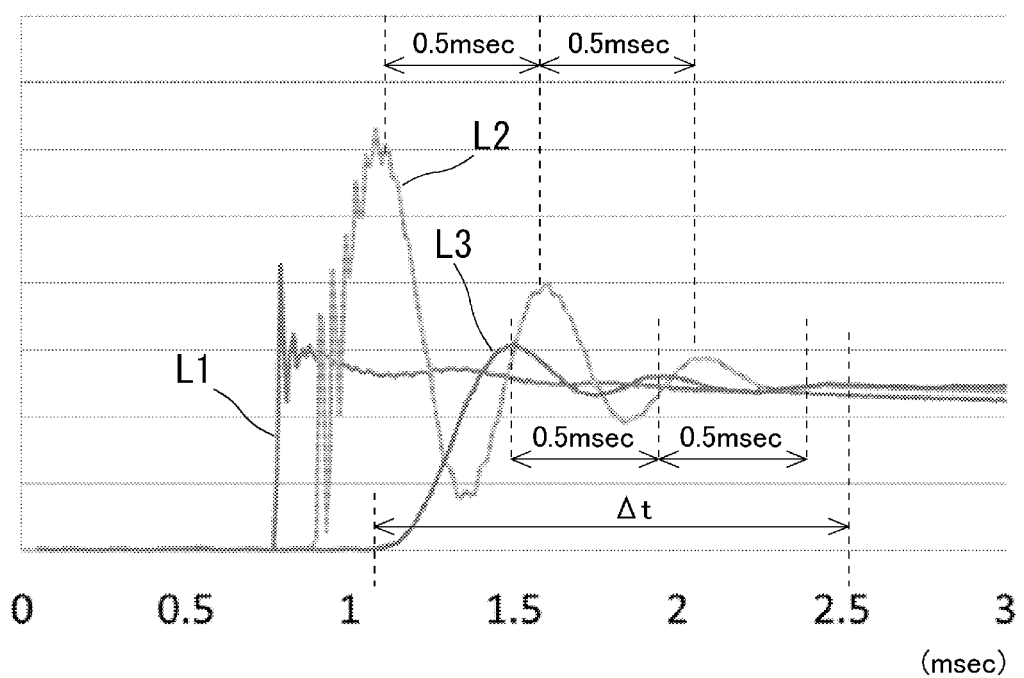
FIG. 5 is a diagram showing respective transitions of combustion pressure related to powder combustion, pressure applied to a sealed dosing liquid, and injection pressure of an injected dosing liquid in the administration apparatus shown in FIG. 1.

Moreover, the total amplitude of each of the vibration elements S2 to S4 other than the first vibration element S1 in the pressure vibration in the injection pressure transition in the prescribed period of time Δt is favorably equal to or lower than a total amplitude value that is used as a reference. As a result, unnecessary dynamic action on cell membrane due to an excessively large total amplitude can be avoided.

Furthermore, the present inventors have focused on the fact that, in the pressure transition indicating a damped vibration within the prescribed period of time Δt, the peak value of the first vibration element S1 is relatively higher than those of the second, third, and fourth vibration elements S2 to S4. When an initial rise of injection pressure is an instantaneous pressure vibration element such as the first vibration element S1 described above, a minute distortion is created between cell membranes, thereby enabling forces directly acting on the cell membranes themselves to be suppressed while effectively canceling out the bonding force created by the bonding means described earlier. In other words, an instantaneous variation in injection pressure by the first vibration element S1 conceivably exerts dynamic action on the object region so as to mutually shift cells and to make it easier for the dosing liquid to flow along interfaces between the cells, and enables unnecessary dynamic action applied to cell membranes themselves to be suppressed. However, since the dynamic action to the cell membranes themselves conceivably becomes non-negligible when the peak value Px1 of the first vibration element S1 is excessively large, in consideration of minimal invasiveness, a prescribed upper limit ratio is favorably set for the peak value Px1 based on peak values of other vibrations (for example, the peak value Px2 of the second vibration element S2 which is a next highest peak value). Therefore, in the present embodiment, the ratio is a value larger than 1 and lower than the prescribed upper limit ratio.

Based on the above, minimal invasiveness of the dosing liquid during administration can be demonstrated based on the fact that, in a transition of pressure (injection pressure) of the dosing liquid entering the object region in an initial stage of administration, the injection pressure vibrates in a damped manner and a peak value of the initial first vibration element S1 in vibrations of the injection pressure becomes larger within a range of a ratio larger than 1 and smaller than the prescribed upper limit ratio relative to peak values of other vibration elements (S2 to S4). The present inventors do not consider both conditions to be requisites in the transition of injection pressure for realizing minimally invasive administration. Minimally invasive administration can conceivably be realized by adopting any one of the conditions. However, more preferable minimally invasive administration can be realized by adopting both conditions in the transition of injection pressure.

Once the prescribed period of time Δt lapses, combustion of the gas generating agent is started by a combustion product of the ignition charge. As a result, the injection pressure of the dosing liquid of which pressure vibration had generally converged rises once again and the peak value Py described earlier arrives. Due to such pressurization of the dosing liquid by the gas generating agent, the dosing liquid having entered the object region at minimal invasiveness can be further diffused inside the object region in an effective manner.

In addition, even when the purpose of administration by the administration apparatus 1 is to introduce a prescribed substance to the inside of cells, a minimally invasive introduction of the substance into the cells can be achieved by adopting at least one of the two conditions described above in an injection pressure transition. Conceivably, by making the peak value of a first vibration element which is an initial vibration element in a group of vibration elements within the prescribed period of time Δt a steep peak value or by setting a frequency of the group of vibration elements to a frequency that belongs to the prescribed frequency range described earlier, at the same time as the entry of dosing liquid into the object region, cell membranes are pressurized over a wide range by the dosing liquid at a faster rate than a propagation of distortion through cells inside the object region and gaps are temporarily created in the cell membranes and, as a result, the introduction of the substance into the cells in a minimally invasive manner is promoted.

Moreover, instead of an aspect in which the peak value of the first vibration element which is an initial vibration element in pressure vibration within the prescribed period of time Δt is set using a peak value of other vibration elements (for example, the second vibration element) as a reference as described above, the peak value of the first vibration element or a flow rate corresponding to the peak value may be set higher than reference injection pressure or a reference flow rate set independently of parameters of the pressure vibration in the prescribed period of time Δt. The reference injection pressure or the reference flow rate may be appropriately changed in accordance with an object region to be an object of administration. For example, when the object region is an organ such as a liver or the heart, according to the minimal invasiveness provided by the present embodiment, a prescribed substance can be administered to tissue that does not constitute blood vessels in the organ while minimizing the effect on the blood vessels in the organ.

Administration with minimal invasiveness is particularly useful for organs that contain a large amount of blood vessels such as the livers. In consideration thereof, the reference injection pressure and the reference flow rate described above are set so that minimal invasiveness on the blood vessels in organs can be achieved.

The formation of an injection pressure transition which enables minimally invasive administration to be performed by the administration apparatus 1 will now be described with reference to FIG. 5. In FIG. 5, an abscissa represents elapsed time in milliseconds and an ordinate represents pressure in MPa. In addition, in FIG. 5, a line L1 represents a transition of pressure inside the through-hole 64 in the administration apparatus 1, a line L2 represents a pressure transition of the dosing liquid 320 stored inside the filling chamber 32, and a line L3 represents injection pressure of the dosing liquid 320. Moreover, with respect to pressure values of the injection pressure transition of the dosing liquid 320, 50% values of original values are displayed so as to overlap with other pressure transitions (lines L1 and L2). Furthermore, the pressure inside the through-hole 64 is measured by installing a pressure sensor to a pressure measurement port provided so as to be connected to the through-hole 64, and pressure of the dosing liquid inside the filling chamber 32 is measured by installing a pressure sensor to a pressure measurement port provided so as to be connected to the filling chamber 32.

As is evident from the pressure transitions, initially, pressure inside the through-hole 64 rises abruptly as the ignition charge of the igniter 71 burns. As the pressure rises, the piston 5 is propelled so as to push the plunger 4, and the dosing liquid is pressurized via the plunger 4. The pressure of the dosing liquid inside the filling chamber 32 due to the pressurization rises somewhat earlier than a rising time of injection pressure as indicated by the line L2, but exhibits a transition that is more or less steep as or even steeper than the rise of the injection pressure, and a subsequent pressure vibration exhibits a damped vibration at generally the same period as the injection pressure transition and at a generally constant frequency. In other words, in the example shown in FIG. 5, the injection pressure transition reaches a converged state in the prescribed period of time $\Delta t$ of approximately 1.5 milliseconds. In addition, since the dosing liquid pressurized in this manner is injected from the injection port 31a, a series of operations for the combustion of the ignition charge, propelling of the piston and pressurization by the plunger in the administration apparatus 1 constitutes a pressurization operation for forming the injection pressure transition shown in FIG. 4A and FIG. 4B.

The prescribed substance that is administered into the object region by the administration apparatus 1 will now be further described. When the prescribed substance is a substance which undergoes a change in physical properties when pressurized inside a liquid medium, efficiency of introduction of the substance into the object region can be enhancing using a reaction of the change. For example, Japanese Patent Application Laid-open No. 2003-261777 discloses a technique of forming a particulate hydrogel by placing polyvinyl alcohol and a water-soluble natural product capable of hydrogen bonding under high pressure. Under high pressure, since a hydroxyl group, an amino group, and a carboxylic group of the natural product bond to generate a microscopic hydrogen-bonded assembly, a three-dimensional molecular structure changes and may enable the natural product to more readily pass through membranes. In consideration thereof, using this characteristic of membrane permeability improvement due to pressure, administering the natural product with the administration apparatus 1 enables the prescribed substance to reach the inside of the object region in an efficient manner. In addition, when pressurization causes a reaction related to the prescribed substance to accelerate, the substance after the reaction can be introduced into the object region.

<Configuration of Design System>

Schematic configurations of a design system 200 for the administration apparatus 1 and an administration system according to the present embodiment will be described with reference to FIG. 6. The design system 200 is a system for calculating design specification information which is related to the administration apparatus 1 and which is necessary for the purpose of administration by the administration apparatus 1 described heretofore. In addition, for example, the information related to the requested purpose of administration is to be input to the design system 200 by a user (for example, a medical professional) of the administration apparatus 1. Furthermore, there may be cases where the information is input by another person (for example, a person designing an administration apparatus) so as to reflect information from the user of the administration apparatus 1. Therefore, the design system 200 can also be described as a system of which input information is information on a user's request related to the purpose of administration and of which output information is design specification information of the administration apparatus 1 necessary for realizing the request.

Moreover, in the present embodiment, the design system 200 is configured to calculate design specification information respectively corresponding to three administration apparatuses 1a to 1c (hereinafter, when there is no need to make an individual reference to an administration apparatus, simply referred to as the administration apparatus 1) with different regions to be an administration object of a dosing liquid. Three administration apparatuses are exemplified in this manner because, when regions to be administration objects differ from each other as in the case of a liver, the heart, the skin, and the like, there is a unique user's request (purpose of administration) for each region. For this reason, in order to realize more preferable administration, a calculation map to be described later is favorably held for roughly each administration object region and utilized to calculate design specification information. Therefore, in the present embodiment, when calculating design specification information, one of the administration apparatuses 1a to 1c must be specified as an administration apparatus to be an object of calculation. The specified administration apparatus corresponds to the object administration apparatus according to the present embodiment.

Figure 6:
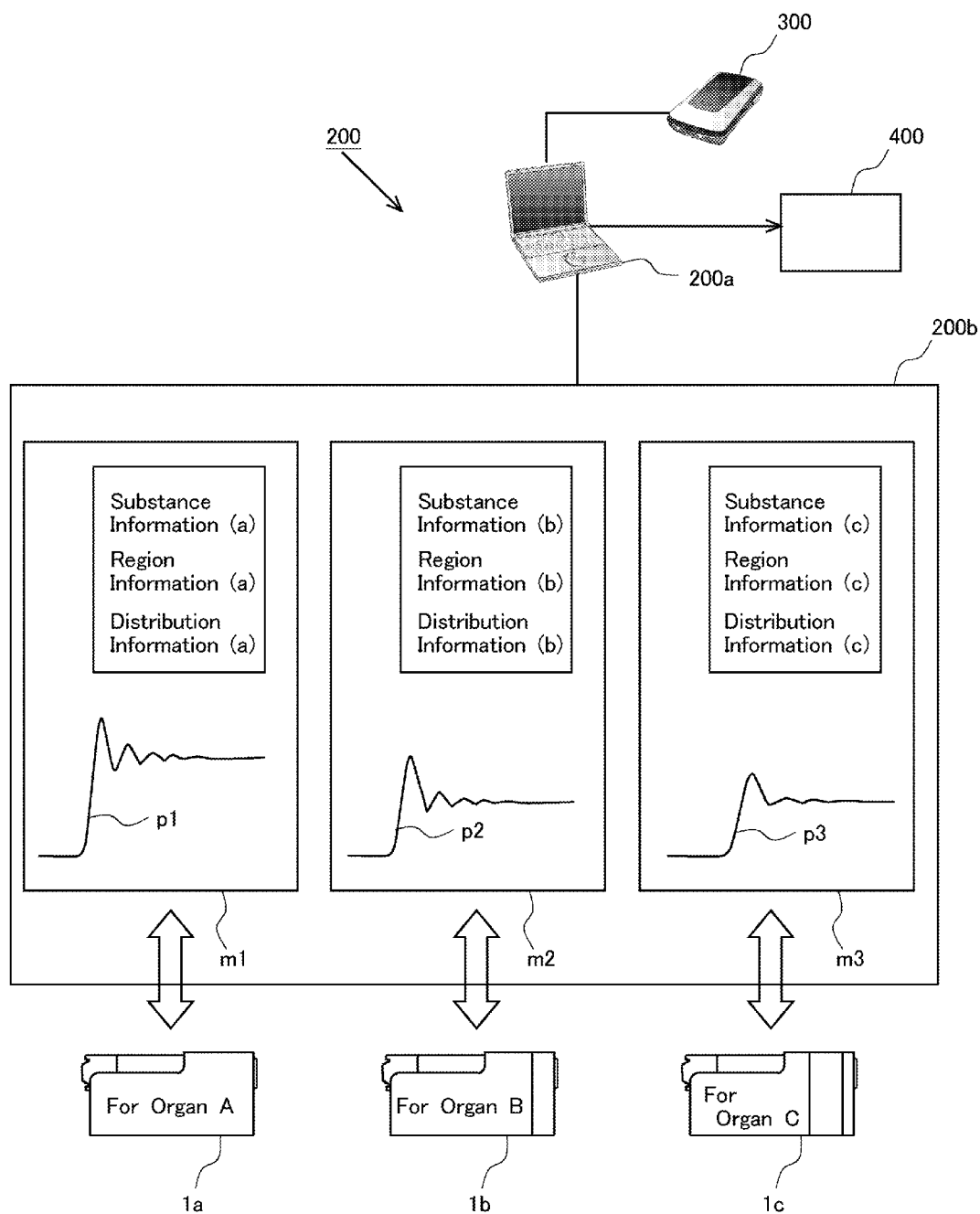
FIG. 6 is a diagram showing a schematic configuration of an administration apparatus design system according to the described technology.

As shown in FIG. 6, the design system 200 has a processing apparatus 200a and a calculation map storage unit 200b. The processing apparatus 200a is an apparatus to which the request information described above is input and which calculates and outputs the design specification information based on the request information. Specific contents of processing will be described later with reference to FIG. 7. In addition, the calculation map storage unit 200b is a so-called memory which corresponds to the map information holding unit according to the present embodiment, and the calculation map storage unit 200b is electrically connected so as to be accessible by the processing apparatus 200a when calculating design specification information.

First, input information and output information will be described. As described above, input information is request information related to the user's purpose of administration and, in the present embodiment, input information is classified into three types, namely, substance information, region information, and distribution information. These pieces of information are set from the perspective of how efficacy and the like of a prescribed substance contained in a dosing liquid can be efficiently exhibited in an administration object region when the user uses the administration apparatus 1. Hereinafter, each piece of information will be described.

(1) Substance Information

Substance information refers to information related to a prescribed substance which characteristically exhibits efficacy and the like desired by the user. Examples of substance information include information related to a drug contained in a dosing liquid, a concentration, a viscosity, or a density of the drug in the dosing liquid, and a specific heat, a dose (a dosing liquid amount), a temperature, a bulk modulus of elasticity, or the like of the dosing liquid. In addition, the prescribed substance is not limited to drugs and may be another substance in a liquid or solid state such as a physiologically active substance for regenerative medicine. The substance information includes not only information related to the prescribed substance such as a drug but also information related to a mixture (such as a dosing liquid) which is formed as a result of the prescribed substance being mixed with a solvent. The specific pieces of information described above are merely examples which need not necessarily be included in the substance information, and the substance information may include apart of these pieces of information or may include other information related to the prescribed substance. As described above, substance information is information having a correlation to behavior of the prescribed substance in the object region after administration and is also information necessary for realizing efficacy and the like requested by the user. Furthermore, conceivably, the injection pressure transition described above which represents an administration capability of the administration apparatus 1 must be adjusted in order to realize the efficacy and the like requested by the user. In consideration thereof, substance information is set as a piece of input information.

Substance information can be measured using existing measurement techniques. For example, a bulk modulus of elasticity that is a piece of substance information is a parameter defined as an inverse of compressibility that is a rate of volume change when pressure is applied to the dosing liquid. In consideration thereof, a bulk modulus of elasticity (K) can be roughly calculated according to the following equation based on a sound velocity (c) corresponding to a temperature of the dosing liquid at the time of administration of the dosing liquid and a density (ρ) of the dosing liquid.

$$K=c^2 \times \rho$$

For the measurement of the density of the dosing liquid and the sound velocity, an apparatus capable of simultaneously measuring both parameters such as the Density and Sound Velocity Meter DSA 5000 M manufactured by Anton Paar Japan K.K. is favorably used.

As an alternative method of calculating the bulk modulus of elasticity (K), the bulk modulus of elasticity (K) can also be calculated according to the following equation in which P denotes pressure applied to the dosing liquid and ε denotes a bulk strain of the dosing liquid upon application of P.

$$K=P/\varepsilon$$

(2) Region Information

Region information refers to information related to an object region to which a dosing liquid containing a prescribed substance which characteristically exhibits efficacy and the like desired by the user is administered. Examples of region information include information related to an organ/system (an eye, the heart, a liver, or the like), bones, teeth, or the like of a living organism that is an administration object region, and a physical parameter or the like related to a hardness of a superficial layer of the administration object region or a degree of diffusion of the dosing liquid inside the administration object region. More specifically, examples include the Young's modulus, the Poisson's ratio, a physical quantity related to softness, elongation at fracture, a modulus of elasticity, a yield strength, stress relaxation (shear stress relaxation, compressive stress relaxation), and a density of the object region to which the dosing liquid is to be administered, a thickness of the object region in a direction of administration, information related to a layer structure of the object region, and a type or the like of cells contained in the object region. The specific pieces of information described above are merely examples which need not necessarily be included in the region information, and the region information may include a part of these pieces of information or may include other information related to the administration object region. In addition, when the administration object region is related to a living organism, region information related to the region may include so-called individual variability and, depending on the request by the user, administration must be performed with adequate consideration of such individual variability. In consideration thereof, information related to individual variability may also be included in the region information. Examples of individual variability information include age, gender, race, weight, and the like of a living organism to be an administration object. As described above, region information is information related to an administration object region in which manifestation of efficacy or the like of the prescribed substance is desired and also information related to a region in which an injected dosing liquid is to enter and be diffused therein. Conceivably, the injection pressure transition described above which represents an administration capability of the administration apparatus 1 must be adjusted in order to further ensure the behavior of the dosing liquid. In consideration thereof, region information is set as a piece of input information.

Region information can be measured using existing measurement techniques. For example, with respect to the Young's modulus of the object region which is a piece of region information, a suction method in which the Young's modulus is calculated by subjecting the object region to suction for a certain amount of time from an opening at a tip of a measurement probe and measuring a displacement of the object region in a subsequent open state, a depression method in which the Young's modulus is calculated by depressing the object region at a constant rate and measuring a reaction force during the depression, and an air-jet method (Makio, Tadashi, Ryoko Oguri, Osamu Kuwazuru, and Kukizo Miyamoto, "Development of Young's Modulus Measurement for Human Skin Epidermis", Transactions of the JSME (in Japanese)) can be used. In addition, with respect to a thickness of the object region, imaging apparatuses using ultrasonic waves can be used. Furthermore, an elongation at fracture, a modulus of elasticity, and a yield strength can be measured by a tensile test or the like prescribed by JIS standards related to a material with similar physical properties to the administration object region (for example, when the administration object region is a skin structure, it is useful to refer to JIS standard K 7312 related to thermosetting polyurethane elastomers). In addition, shear stress relaxation and compressive stress relaxation can be measured using Rheosol-G5000 manufactured by UBM. Furthermore, the Poisson's ratio can be calculated based on a result of measurements of the shear stress relaxation and the compressive stress relaxation. Moreover, with respect to region information, respective physical properties such as the Young's modulus of a model (for example, a model formed by a synthetic polymer such as a gel) which simulates the administration object region can be utilized in place of the physical properties described above of the actual administration object region.

In addition, information disclosed in the following documents is also useful as samples of region information when the object region is a living organism.

Reference 1: Agache P G, Monneur C, Leveque J L, De Rigal J, Mechanical properties and Young's modulus of human skin in vivo., Arch Dermatol Res 269 (3), 1980, 221-232

Reference 2: Yamada H., Evans F. G., (Ed.), Strength of Biological Materials (Book), The Williams & Wilkins Company, 1970

(3) Distribution Information

Distribution information refers to information which is related to a state of distribution of a dosing liquid in an object region to which a prescribed substance is administered and which indicates favorable behavior of the dosing liquid when distributed in the object region. Examples of distribution information include information related to an administration depth of the dosing liquid in the administration object region (an extent of reach of the dosing liquid in a direction approximately perpendicular with respect to a superficial layer of the object region) or a spread of the dosing liquid in the administration object region (an extent of diffusion of the dosing liquid in a direction approximately parallel to the superficial layer of the object region), a degree of invasiveness which is permissible in the administration object region, and information such as a position to be reached by the prescribed substance in the administration object region (in other words, whether the prescribed substance is to be directly introduced into a cell (into a membrane or into a nucleus) or the prescribed substance is to be diffused between cells when administering the prescribed substance to a living organism) or the time required by the prescribed substance to reach a reached position after entering the administration object region from the superficial layer. The specific pieces of information described above are merely examples which need not necessarily be included in the distribution information, and the distribution information may include a part of these pieces of information or may include other information related to a distribution in the administration object region. As described above, since distribution information is information related to a distribution of the dosing liquid in an administration object region which is necessary for causing efficacy or the like desired by the user to be manifested in an efficient manner and which significantly affects an effect of administration by the administration apparatus 1, conceivably, the injection pressure transition described above which represents an administration capability of the administration apparatus 1 must be adjusted. In consideration thereof, distribution information is set as a piece of input information.

Moreover, while the three pieces of information described above are adopted as input information in the present embodiment, a part of the three pieces of information may be adopted as input information or other information may be additionally adopted as input information insofar as administration by the administration apparatus 1 can be supported more effectively. What is of paramount importance in the present embodiment is that information useful for improving the effect of administration by the administration apparatus 1 is not impeded from being appropriately adopted as input information.

Next, output information will be described. As described earlier, output information refers to information related to design specifications of the administration apparatus 1 necessary for realizing the user's request and, specifically, refers to information related to design specifications of a component of the administration apparatus 1 which adjusts the injection pressure transition described earlier. In particular, information directly related to the injection pressure transition is information related to an ignition charge included in the igniter 71 (which corresponds to the energy information according to the present embodiment and which is hereinafter referred to as "gunpowder information"). In consideration thereof, in the present embodiment, design specification information includes at least gunpowder information and may additionally include information related to dimensions or a shape of respective parts (the syringe section 3, the plunger 4, the piston 5, and the administration apparatus main body 6) and the like which constitute the administration apparatus 1.

Examples of gunpowder information include a type, a loaded amount, or a shape of the ignition charge, and a presence or absence of a gas generating agent. When a gas generating agent is used, gunpowder information may further include a type, a loaded amount, a shape, or the like of the gas generating agent. In addition, examples of design specification information related to the syringe section 3 include a material of the body 30, a shape of the nozzle section 31, a diameter of the injection port 31a, and the number of the injection ports 31a of the syringe section 3. Furthermore, examples of design specification information related to the plunger 4 include a material of the plunger 4 and parameters regarding contact (friction) between the barrel section 42 of the plunger 4 and an inner wall surface of the filling chamber 32 (such as a surface profile of the barrel section 42). Examples of design specification information related to the piston 5 include a piston diameter (in other words, an area of the second barrel section 52 which receives energy generated by combustion of the ignition charge) and parameters regarding contact (friction) between the first barrel section 51 or the second barrel section 52 and an inner wall surface of the through-hole 64. Examples of design specification information related to the administration apparatus main body 6 include an inner space volume, a diameter, or the like of the through-hole 64 through which a combustion product of the ignition charge is released and in which, in some cases, a gas generating agent is to be arranged. The specific pieces of information described above are merely examples which need not necessarily be included in the design specification information, and the design specification information may include a part of these pieces of information or may include other information related to the design specifications of the parts of the administration apparatus 1.

Let us now return to FIG. 6. The calculation map storage unit 200b constituting the design system 200 respectively stores calculation maps m1 to m3 for calculating respective pieces of design specification information of the administration apparatuses 1a to 1c. The calculation map m1 will now be described as an example. The calculation map m1 is a map for calculating design specification information when performing administration to an organ A (for example, a liver). Let us assume that, for example, the organ A characteristically contains a large number of blood vessels and therefore requires minimal invasiveness with respect to the blood vessels. In consideration thereof, a reference injection pressure transition p1 of the dosing liquid capable of realizing minimal invasiveness is set in a standard organ A configured by an experiment, a simulation, or the like carried out in advance. As an example, the injection pressure transition p1 is set using a length of the prescribed period of time Δt described above, a ratio of a peak value of the first vibration element S1 to a peak value of the second vibration element S2, the peak value of the first vibration element S1, a time required to reach the peak value from a rising time of injection pressure, or the like as a parameter. In addition, the calculation map m1 is formed by correlating design specification information for the administration apparatus 1a capable of realizing the reference injection pressure transition p1 with reference input information including substance information, region information, and distribution information corresponding to the reference injection pressure transition p1. In other words, when reference input information in the administration apparatus 1a is set, the calculation map m1 includes design specification information of the administration apparatus 1a which enables the reference injection pressure transition to be realized by the administration apparatus 1a. Favorably, the calculation map m1 includes design specification information corresponding to a plurality of pieces of reference input information. The calculation map m2 for the administration apparatus 1b and the calculation map m3 for the administration apparatus 1c are similar to the calculation map m1.

In addition, in the design system 200, a sensor 300 is connected to the processing apparatus 200a. The sensor 300 is a sensor capable of detecting the Young's modulus related to hardness of the superficial layer of the administration object region included in region information among the pieces of input information described above. For example, the Young's modulus is automatically detected using the suction method or the depression method as described earlier. Information on the hardness of the superficial layer related to the Young's modulus of the administration object region detected in this manner is handed over to the processing apparatus 200a and used as region information in a calculation process of design specification information to be described later. Furthermore, other pieces of input information may be input by the user using an input apparatus (a keyboard, a mouse, or the like) provided in the processing apparatus 200a, or relevant information may be automatically or semi-automatically detected by a detection apparatus which differs from the sensor 300 to be handed over to the processing apparatus 200a.

Furthermore, a preparation apparatus 400 is electrically connected to the processing apparatus 200a. The preparation apparatus 400 is an apparatus which prepares, based on gunpowder information included in the design specification information output by the processing apparatus 200a, gunpowder to be loaded to any of the corresponding administration apparatuses 1a to 1c. For example, the preparation apparatus 400 stores a plurality of igniters for each administration apparatus, and the preparation apparatus 400 is configured to extract an igniter loaded with a most suitable ignition charge in accordance with the gunpowder information from the processing apparatus 200a and provide the user with the extracted igniter. In this case, bodies of the igniters may be painted in a different color for each administration apparatus so that the user can appropriately mount the provided igniter to the corresponding administration apparatus. Moreover, the user can appropriately adjust a configuration of parts of the administration apparatus other than the igniters based on the design specification information output from the processing apparatus 200a.

Figure 7:
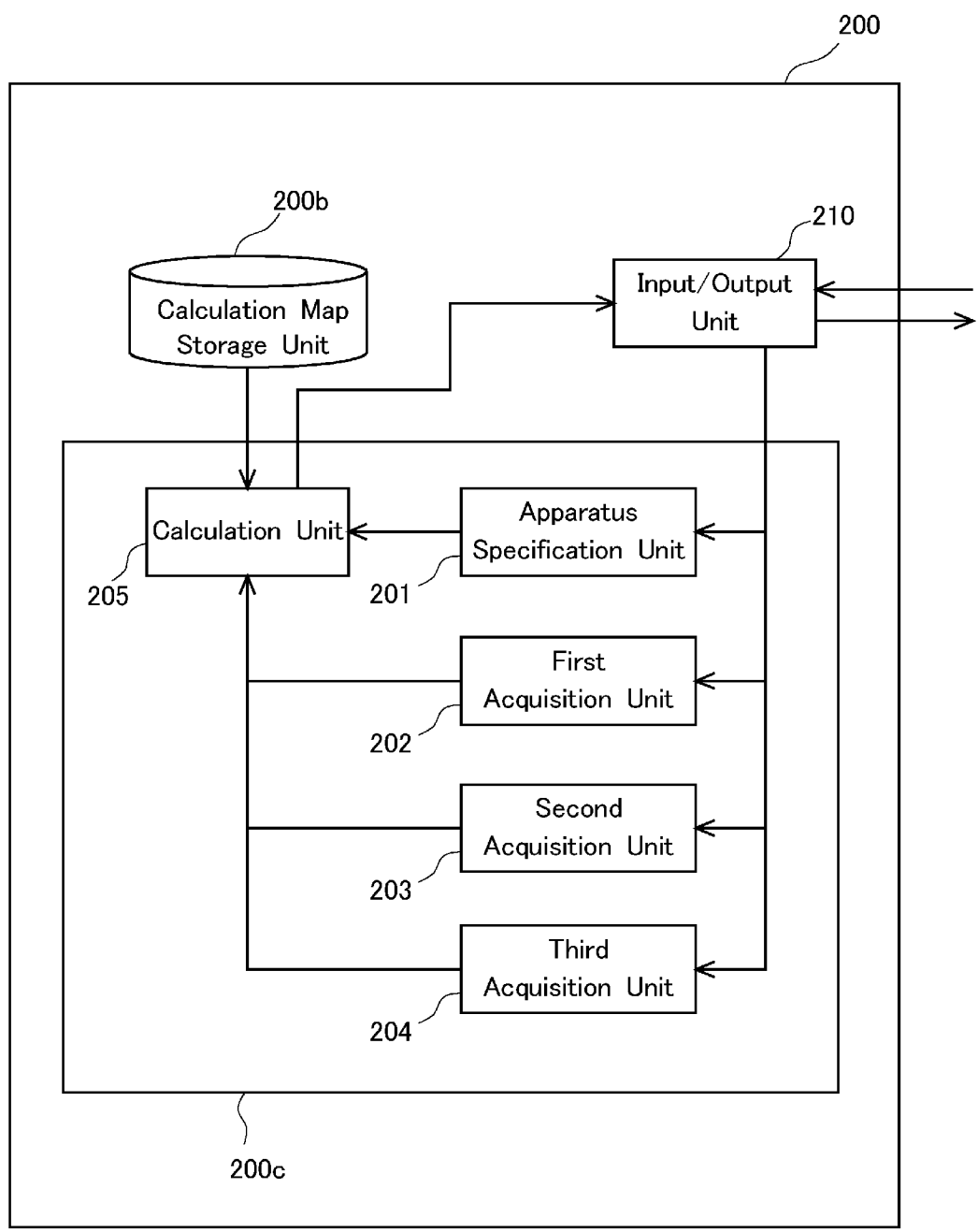
FIG. 7 is a functional block diagram of the design system shown in FIG. 6.
Figure 8:
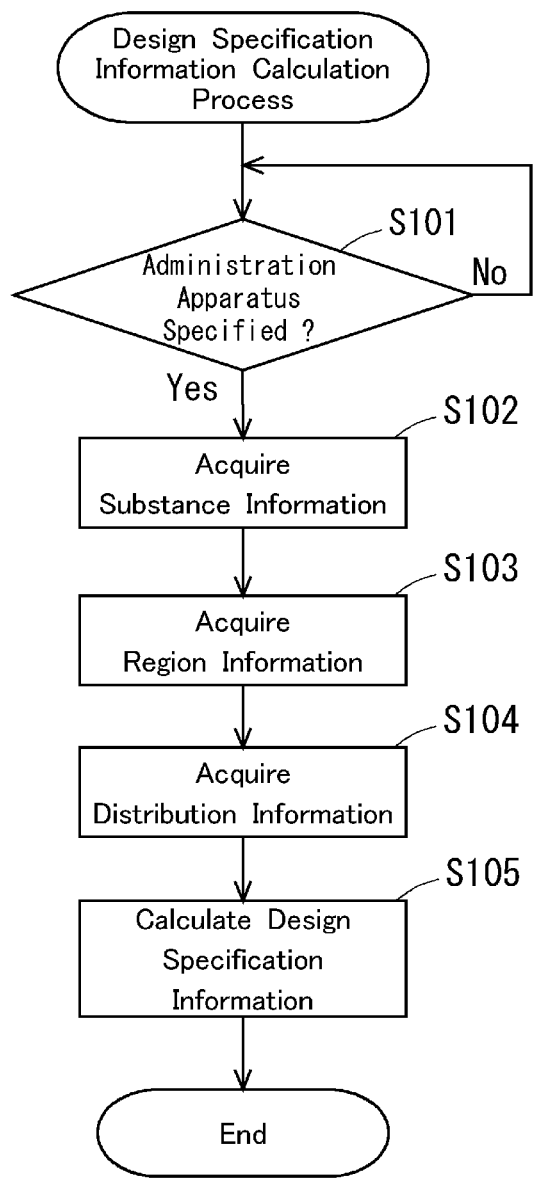
FIG. 8 is a flow chart of a design specification information calculation process executed by the design system shown in FIG. 6.

A calculation process for calculating design specification information by the design system 200 will now be described with reference to FIGS. 7 and 8. FIG. 7 is an imaged diagram of functional units formed in the design system 200 regarding the calculation process. In addition, FIG. 8 is a flow chart of the calculation process. Moreover, the functional units shown in FIG. 7 are formed and the calculating process shown in FIG. 8 is realized as the design system 200 executes a prescribed calculating program using a calculation unit, a memory, and the like in the processing apparatus 200a.

First, functional units of the design system 200 will be described. The design system 200 has a control unit 200c and an input/output unit 210 as functional units, and also includes the calculation map storage unit 200b described earlier. The input/output unit 210 is a functional unit to which is input a request from the user related to efficacy or the like expected by administration by the administration apparatus 1 and, further, which outputs design specification information calculated by the processing apparatus 200a in order to convey the design specification information to the user. The input request information is each of the substance information, the region information, and the distribution information described earlier, and the request information is input by the input apparatus (a keyboard, a mouse, or the like) provided in the processing apparatus 200a as described above or a user's request is input via a prescribed interface from an apparatus that differs from the processing apparatus 200a. In addition, information related to hardness of a superficial layer of an object region detected by the sensor 300 is also input to the input/output unit 210. Output of design specification information includes modes in which a calculation result is displayed on a display apparatus (a display) of the processing apparatus 200a and, when the design specification information is to be used in another processing apparatus outside of the system, a mode in which the design specification information is transmitted to the other processing apparatus as electronic information.

The control unit 200c includes an apparatus specification unit 201, a first acquisition unit 202, a second acquisition unit 203, a third acquisition unit 204, and a calculation unit 205. The apparatus specification unit 201 is a functional unit which specifies, based on information input to the input/output unit 210, an administration apparatus of a type to be a calculation object of design specification information (an apparatus corresponding to the object administration apparatus according to the present embodiment and, in the example shown in FIG. 6, any of the administration apparatuses 1a to 1c). In addition, the first acquisition unit 202, the second acquisition unit 203, and the third acquisition unit 204 are functional units which respectively acquire substance information, region information, and distribution information based on information input to the input/output unit 210. Furthermore, the calculation unit 205 is a functional unit which calculates, in an administration apparatus specified by the apparatus specification unit 201, design specification information related to the specified administration apparatus for realizing a request by the user based on the respective pieces of information acquired by the first acquisition unit 202, the second acquisition unit 203, and the third acquisition unit 204.

A calculation process of design specification information which is realized by cooperation of the respective functional units will be described with reference to FIG. 8. First, in S101, based on the information input to the input/output unit 210, a determination is made on whether or not the user has specified an administration apparatus to be a calculation object of design specification information. The determination is made by the apparatus specification unit 201. When a positive determination is made in S101, the flow proceeds to S102, but when a negative determination is made, the process of S101 is repeated once again. Next, respectively in S102 to S104, substance information is acquired by the first acquisition unit 202, region information is acquired by the second acquisition unit 203, and distribution information is acquired by the third acquisition unit 204. Although the substance information, the region information, and the distribution information are acquired in this order in the flow chart shown in FIG. 8, an order of acquisition of these pieces of input information is not limited to the order shown in FIG. 8. The respective functional units need only acquire corresponding information as appropriate in accordance with an order of input of information by the user.

Once acquisition of the respective pieces of information is completed, in S105, design specification information is calculated by the calculation unit 205. Specifically, with respect to a calculation map corresponding to the administration apparatus specified by the apparatus specification unit 201 among the calculation maps held by the calculation map storage unit 200b, the calculation unit 205 extracts corresponding design specification information using the substance information acquired by the first acquisition unit 202, the region information acquired by the second acquisition unit 203, and the distribution information acquired by the third acquisition unit 204 as arguments. More specifically, when each type of information used as an argument is included as the reference input information described earlier in the calculation map, the calculation unit 205 extracts design specification information corresponding to the reference input information. On the other hand, when the input information used as an argument is not included as the reference input information described earlier in the calculation map, the calculation unit 205 obtains an output by specifying reference input information that is close to the input information used as an argument and interpolating design specification information corresponding to the specified reference input information.

An example of a specific calculation of design specification information will now be described.

Practical Example 1

As a first practical example, an example of a calculation of design specification information of the administration apparatus 1 which administers an influenza vaccine to a human will be described. In the practical example, a type of an administration apparatus to be used is determined based on a dose of the vaccine. Specifically, as shown in Table 1 below, a dose of the vaccine is selected from three doses of 10 μL, 100 μL, and 1000 μL, and the administration apparatuses 1a to 1c are to be used in accordance with the respective doses. For example, when an input indicating a dose of 100 μL is received by the input/output unit 210, the administration apparatus 1b is to be selected as the used administration apparatus. Moreover, a determination process of the used administration apparatus is performed by the apparatus specification unit 201.

TABLE 1

| Administration apparatus to be used | Administration apparatus 1a | Administration apparatus 1b | Administration apparatus 1c |
|---|---|---|---|
| Amount of administration (μL) | 10 μL | 100 μL | 1000 μL |

Next, the substance information acquired by the first acquisition unit 202 in the present practical example is information related to a dosing liquid including the influenza vaccine as shown in Table 2 below.

TABLE 2

| Substance information attribute | Density | Viscosity | Bulk modulus of elasticity |
|---|---|---|---|
| Value | ρ m (g/cm3) | μ (mPa/sec) | K (Mpa) |

In addition, the region information acquired by the second acquisition unit 203 in the present practical example is information related to a human skin structure that is an administration object of the influenza vaccine as shown in Table 3 below.

TABLE 3

| Region information attribute | Thickness | Density | Modulus of elasticity | Poisson's ratio | Stress relaxation time |
|---|---|---|---|---|---|
| Value | Ts (mm) | ρ s (g/cm3) | Es (Mpa) | σ s | τ s (sec) |

Furthermore, the distribution information acquired by the third acquisition unit 204 in the present practical example is information related to a movement of the dosing liquid in a human skin structure as shown in Table 4 below.

TABLE 4

| Distribution information attribute | Administration depth | Spread |
|---|---|---|
| Value | D (mm) | W (mm) |

While the calculation unit 205 calculates design specification information based on the acquired substance information, region information, and distribution information, the calculation unit 205 calculates the design specification information using a calculation map included in the calculation map storage unit 200b. Generation of the calculation map will now be described. First, a simulator was constructed in order to generate the calculation map. The simulator is a simulator which is based on mechanics and fluid mechanics and which uses a finite element method, and which is capable of tracking a mechanical behavior of each member of the administration apparatus 1 and a hydrodynamic behavior of a dosing liquid ranging from combustion of gunpowder in an igniter used in the administration apparatus, generation of pressure by the combustion of gunpowder, driving of the piston and the plunger by the generated pressure generated by the combustion of gunpowder, pressurization of the dosing liquid by the plunger, injection of the dosing liquid from a nozzle by the pressurization, to penetration in a depth direction and spread in a horizontal direction of the injected dosing liquid in a skin structure. The simulator is constructed using 10,000 scientific/technological computers powered by CPUs (64 core) manufactured by Intel Corporation.

From a mathematical perspective, the simulator can be regarded as a function of several variables which includes design specification information as an argument, which further includes, as arguments, the substance information and the region information described earlier that affect driving of components of the administration apparatus such as the piston and an administration depth and a spread of the injected dosing liquid in the object region, and which determines an administration depth D and a spread W as the distribution information described earlier. In consideration thereof, processing performed by the simulator may be mathematically expressed as follows.

$$\text{Administration depth } D = D((m_Z, V_{in}, m_{pl}, d_{out}), (\rho_m, \mu, K), (t_s, \rho_s, E_s, \sigma_s, \tau_s))$$

$$\text{Spread } W = W((m_Z, V_{in}, m_{pl}, d_{out}), (\rho_m, \mu, K), (t_s, \rho_s, E_s, \sigma_s, \tau_s))$$

In this case, $m_Z$ denotes a loaded amount of gunpowder that is a high-energy substance, and information related to the amount of gunpowder corresponds to the gunpowder information according to the present embodiment. In addition, $V_{in}$ denotes a volume of the through-hole 64 that is a combustion chamber and represents design specification information related to the administration apparatus main body 6. Furthermore, $m_{pl}$ denotes a mass of the plunger 4 and the piston 5 and represents design specification information related to the plunger 4 and the piston 5. Moreover, $d_{out}$ denotes a diameter of the injection port 31*a* and represents design specification information related to the syringe section 3.

Next, a calculation map generation method using the simulator will be described. With respect to the parameters of design specification information, substance information, and region information described above, the administration depth D and the spread W which are pieces of distribution information created by the simulator are calculated at sampling points shown in Table 5 below. In addition, a lower field of Table 5 describes the number of samplings for each parameter. According to the numbers of samplings, the number of simulation results for all parameters is approximately 224 million points.

The administration depth D and the spread W which represent the simulation result correspond to distribution information. Therefore, a calculation map can be generated by combining the calculated distribution information with the substance information ($\rho_m$, $\mu$, K) and the region information ($t_s$, $\rho_s$, $E_s$, $\sigma_s$, $\tau_s$) shown in Table 5 and, at the same time, associating the combined information with the design support information ($m_Z$, $V_{in}$, $m_{pl}$, $d_{out}$) which is also shown in Table 5. The generated calculation map is stored in the calculation map storage unit 200*b*. The calculation map is generated for each of the administration apparatuses 1*a* to 1*c*.

Design support information corresponding to a selected administration apparatus is to be calculated by the calculation unit 205 by accessing, using the substance information, the region information, and the distribution information acquired from the respective acquisition units as arguments, the calculation map generated as described above. Specifically, the calculation unit 205 selects, from a calculation map corresponding to the administration apparatus determined based on an input dose, a sampling point in accordance with each of the substance information, the region information, and the distribution information acquired from the respective acquisition units by applying a sorting algorithm using the pieces of information as arguments. Subsequently, design specification information corresponding to the sampling point is derived.

Practical Example 2

While a calculation method of design specification information using a calculation map has been shown in the first practical example described above, in a second practical example, an example will be described in which functions of the simulator described above for calculating the adminis-

TABLE 5

| | Design Specification Information | | | |
|---|---|---|---|---|
| Attribute | Fill amount of gunpowder | Volume of comustion chamber | Weight of plunger and piston | Diameter of injection port |
| Value | mz (mg) | Vin (cm3) | mpl (g) | dout (mm) |
| Sampling range | mzlow-mzupper | Vinlow-Vinupper | mpllow-mplupper | doutlow-doutupper |
| Sampling numbers | 8 | 3 | 3 | 3 |

| | Substance Information | | |
|---|---|---|---|
| Attribute | Density | Viscosity | Bulk modulus of elasticity |
| Value | ρ m (g/cm3) | μ (mPa/sec) | K (Mpa) |
| Sampling range | ρ mlow-ρ mupper | μ low-μ upper | Klow-Kupper |
| Sampling numbers | 3 | 11 | 5 |

| | Region Information | | | | |
|---|---|---|---|---|---|
| Attribute | Thickness | Density | Modulus of elasticity | Poisson's ratio | Stress relaxation time |
| Value | ts (mm) | ρ s (g/cm3) | Es (Mpa) | σ s | τ s (sec) |
| Sampling range | tslow-tsupper | ρ slow-ρ supper | Eslow-Esupper | σ slow-σ supper | τ slow-τ supper |
| Sampling numbers | 21 | 4 | 5 | 3 | 3 | tration depth D and the spread W which represent distribution information are directly used instead to calculate design specification information. As described above, the administration depth D and the spread W can be expressed as functions of several variables having substance information and region information as parameters and using design specification information as an argument as shown below.

Administration depth $D=D((m_Z,V_{in},m_{pl},d_{out}),(\rho_m,\mu,K)(t_s,\rho_s,E_s,\sigma_s,T_s))$ Spread $W=W((m_Z,V_{in},m_{pl},d_{out})(\rho_m,\mu,K)(t_s,\rho_s,E_s,\sigma_s,T_s))$ Let Dobj and Wobj respectively denote values of the administration depth and the spread which represent distribution information acquired by the third acquisition unit 204. In addition, when calculating design specification information, $m_Z$, $V_{in}$, $m_{pl}$, and $d_{out}$ which represent design specification information may be optimized using a least squares method so that the administration depth D and the spread W obtained by the functions of several variables given above approach Dobj and Wobj. Specifically, an evaluation function F of a least squares method is set as follows.

$F=w1(D-\text{Dobj})^2 w2(W-\text{Wobj})^2$ w1 and w2 denote weights in the evaluation function F and may be set as appropriate. Subsequently, a set of points $m_Z$, $V_{in}$, $m_{pl}$, and $d_{out}$ related to the design specification information which provides an extremum of the evaluation function F is determined using, for example, a steepest descent method or a conjugate gradient method so as to minimize a value of the evaluation function F. When a calculation of the design specification information is performed by the calculation unit 205 using functions of the simulator in this manner, calculation accuracy can be generally improved as compared to cases where the design specification information is calculated using the calculation map described in the practical example 1.

A loaded amount $m_Z$ of gunpowder which represents gunpowder information in the design specification information calculated according to the practical examples 1 and 2 will now be described. For example, in the distribution information acquired by the third acquisition unit 204, the deeper the requested administration depth D, the larger the loaded amount $m_Z$ of the ignition charge so that the first vibration element S1 among the injection pressure transition described earlier has a higher peak value.

Moreover, while the distribution information does not include a degree of invasiveness permissible in the administration object region as a parameter in the practical examples 1 and 2, constructing a simulator so that the distribution information includes a degree of the invasiveness in a similar manner to the administration depth and the spread described above enables design specification information capable of realizing the degree of invasiveness requested by the user to be calculated. In addition, when the requested degree of invasiveness is high (for example, when diffusion of the dosing liquid with lower invasiveness is requested), for example, the loaded amount $m_Z$ of the ignition charge, the diameter dout of the injection port 31a, or the like is calculated as to shorten the time required to reach the peak value of the first vibration element S1 in the injection pressure transition described above. Furthermore, related design specification information may be calculated so as to further shorten the prescribed period of time Δt.

As described above, with the design system 200 according to the present embodiment, an administration effect by the administration apparatus 1 which is requested by the user can be realized more readily and in a preferable manner. In addition, as shown in FIG. 6, by connecting the processing apparatus 200a of the design system 200 with the preparation apparatus 400, the user can readily obtain a preferable igniter corresponding to the user's request.

<Modification 1>

Figure 9:
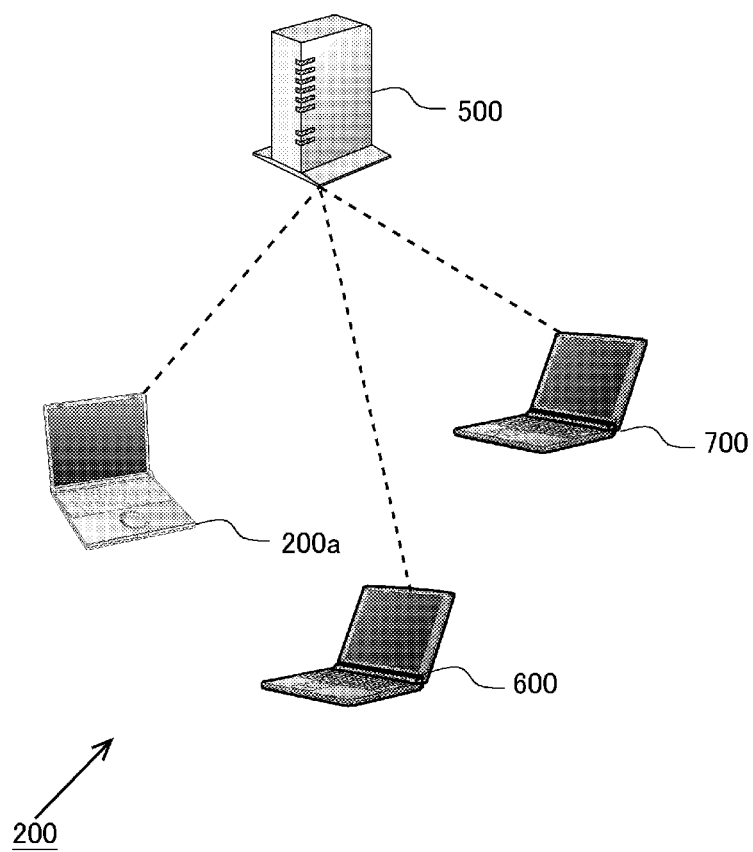
FIG. 9 is a diagram showing another aspect of the administration apparatus design system according to the described technology.

FIG. 9 shows a modification of the design system 200. In the present modification, the function of the control unit 200c and the function of the calculation map storage unit 200b shown in FIG. 7 are consolidated in a processing server 500. In addition, the respective processing apparatuses 200a, 600, and 700 retain the function of the input/output unit 210 shown in FIG. 7. A request from the user is input to the respective processing apparatuses 200a, 600, and 700 and transmitted to the processing server 500. Subsequently, based on the transmitted apparatus specification information and input information, the processing server 500 calculates design specification information corresponding to the specified administration apparatus and once again transmits the design specification information to a corresponding processing apparatus. The processing apparatus to which the design specification information had been transmitted outputs a result thereof to the user via a display or the like. By collectively calculating design specification information with a processing server, design specification information of an administration apparatus in a large-scale medical setting such as a hospital can be readily calculated and convenience of a user can conceivably be improved. Moreover, transmission of information between the respective processing apparatuses 200a, 600, and 700 and the processing server 500 may be performed in a wireless manner or a wired manner.

<Modification 2>

While the design system 200 related to an administration apparatus which uses gunpowder as a power source is disclosed in the embodiment described above, the described technology can also be applied to other administration apparatuses which use gunpowder as a power source, and a design system for such administration apparatuses can constructed. An example of such an administration apparatus is an apparatus which introduces a biologically-derived substance to a cell using gunpowder as a power source, and administration of a substance using the injection pressure transition described earlier can also be performed in this case. The described technology can also be applied to a system configuration for calculating design specification information of such an administration apparatus. Examples of such an administration apparatus include an apparatus for seeding cultured cells, stem cells, or the like to cells or scaffold tissue/scaffolds which are administration objects for the purpose of regenerative medicine with respect to humans. For example, as described in Japanese Patent Application Laid-open No. 2008-206477, cells which can be appropriately determined by a person skilled in the art in accordance with a site of implantation and a purpose of recellularization such as endothelial cells, endothelial progenitor cells, bone marrow cells, preosteoblasts, chondrocytes, fibroblasts, skin cells, muscle cells, liver cells, kidney cells, intestinal cells, stem cells, and any other cells considered in the field of regenerative medicine may be administered.

In addition, the described technology can also be applied in order to calculate design specification information of an administration apparatus which delivers DNA or the like to cells, scaffold tissue/scaffolds, and the like such as described in Japanese Translation of PCT Application No. 2007-525192. Furthermore, the described technology can also be applied in order to calculate design specification information of an apparatus which directly delivers various genes, cancer suppressor cells, a lipid envelope, or the like to object tissue or which administers an antigen gene in order to improve immunity to pathogens. Moreover, the described technology can also be applied in order to calculate design specification information of an administration apparatus which can be used in various fields of disease treatment (the fields described in Japanese Translation of PCT Application No. 2008-508881, Japanese Translation of PCT Application No. 2010-503616, and the like), the field of immunological medicine (the field described in Japanese Translation of PCT Application No. 2005-523679), and the like.

<Modification 3>

Examples of an administration apparatus using the injection pressure transition described earlier include a catheter apparatus. A catheter apparatus is an apparatus which has a catheter unit capable of entering a living organism and which administers a desired drug solution or the like to the living organism from a tip section of the catheter unit. The described technology can be applied to a configuration for the administration of a drug solution from the tip section of the catheter unit. In other words, in a state where the catheter unit has entered inside the living organism, by controlling injection pressure of a drug solution to match the characteristic injection pressure transition according to the described technology described earlier when administering the drug solution from the tip section of the catheter unit, a minimally invasive administration of the drug solution to a prescribed site of an object region (for example, an internal organ such as the heart or a liver) to which the drug solution is to be administered can be achieved. The technical concepts disclosed with respect to the design system according to the described technology can be applied to calculate design specification information of such a catheter apparatus.

Reference Example

The technical concepts disclosed with respect to the design system according to the described technology can also be applied to administration apparatuses which utilize energy other than the combustion energy of a high-energy substance. For example, using the technical concepts of the described technology, design specification information of an administration apparatus using energy of a spring, compressed gas, or the like can be calculated based on substance information related to a dosing liquid (an administration object substance), region information related to an object region, and distribution information related to a distribution state. The design specification information in this case include information on the spring, the compressed gas, or the like (for example, a compression amount of the spring or a pressure accumulation value of the compressed gas) which is a driving source to be used to administer a dosing liquid.

The invention claimed is:

1. An administration apparatus design system for calculating design specifications of an administration apparatus configured to administer an administration object substance to an object region using gunpowder as a driving source, the system comprising:
    an apparatus specification unit configured to specify the administration apparatus for which the design specifications are to be calculated, as an object administration apparatus;
    a first acquisition unit configured to acquire substance information related to a prescribed administration object substance to be administered in the object administration apparatus;
    a second acquisition unit configured to acquire region information related to a prescribed object region to which the prescribed administration object substance is to be administered;
    a third acquisition unit configured to acquire distribution information related to a distribution state of the prescribed administration object substance, the distribution state being anticipated to be formed in the prescribed object region when the prescribed administration object substance is administered by the object administration apparatus; and
    a calculation unit configured to calculate, based on the substance information acquired by the first acquisition unit, the region information acquired by the second acquisition unit, and the distribution information acquired by the third acquisition unit, design specification information related to a configuration of the object administration apparatus including information regarding the gunpowder to administer the prescribed administration object sub stance.

2. The administration apparatus design system according to claim 1, wherein:
    the administration apparatus is configured to administer the administration object substance into the object region by injecting the administration object substance toward the object region using the gunpowder as the driving source and causing the administration object substance to penetrate a superficial layer of the object region, without involving an introduction unit which introduces the administration object substance into the object region.

3. The administration apparatus design system according to claim 1, further comprising:
    an object region sensor configured to detect a prescribed physical parameter related to a hardness of a superficial layer of the prescribed object region,
    wherein the second acquisition unit is configured to acquire, as at least a part of the region information, the prescribed physical parameter detected by the object region sensor.

4. The administration apparatus design system according to claim 1, further comprising:
    a map information holding unit configured to hold a plurality of calculation maps respectively corresponding to a plurality of types of the administration apparatus and defining a correlation between the substance information, the region information and the distribution information, and the design specification information for each type of administration apparatus,
    wherein the calculation unit is configured to calculate the design specification information based on a calculation map corresponding to the object administration apparatus specified by the apparatus specification unit, among the calculation maps held by the map information holding unit.

5. The administration apparatus design system according to claim 1, wherein the distribution information includes at least one of information related to an administration depth of the administration object substance in the object region and information related to a spread of the administration object substance in the object region.

6. An administration system, comprising:
   the administration apparatus design system according to claim 1;
   the administration apparatus configured to administer the administration object substance to the object region using the gunpowder as the driving source without involving an introduction unit; and
   a preparation apparatus configured to prepare the gunpowder of a type and in a loaded amount that correspond to the object administration apparatus, in accordance with the information regarding the gunpowder included in the design specification information calculated by the calculation unit.

7. The administration apparatus design system according to claim 1, wherein the information regarding the gunpowder comprises at least one of a type of the gunpowder, an amount of the gunpowder configured to be loaded into the object administration apparatus, a shape of an ignition charge, or a presence or absence of a gas generating agent.

8. The administration apparatus design system according to claim 1, wherein the configuration of the object administration apparatus further comprises a dimension or shape of components of the object administration apparatus.

9. The administration apparatus design system according to claim 8, wherein the components comprise a syringe section, an administration apparatus main body, a combustion chamber, a plunger and/or a piston of the object administration apparatus.

10. The administration apparatus design system according to claim 9, wherein the dimension of the object administration apparatus comprises a volume of the combustion chamber.

11. A method of calculating design specifications of an administration apparatus which administers an administration object substance to an object region using gunpowder as a driving source, the method comprising:
    specifying the administration apparatus for which the design specifications are to be calculated, as an object administration apparatus;
    acquiring substance information related to a prescribed administration object substance to be administered in the object administration apparatus;
    acquiring region information related to a prescribed object region to which the prescribed administration object substance is to be administered;
    acquiring distribution information related to a distribution state of the prescribed administration object substance, the distribution state being anticipated to be formed in the prescribed object region when the prescribed administration object substance is administered by the object administration apparatus, the distribution information comprising at least one of a spread of the prescribed administration object substance in the prescribed object region, a degree of invasiveness permissible in the prescribed object region, or a time required by the prescribed administration object substance to reach an intended position of the prescribed object region; and
    calculating, based on the acquired substance information, the acquired region information, and the acquired distribution information, design specification information related to a configuration of the object administration apparatus including information regarding the gunpowder to administer the prescribed administration object substance.

12. The method according to claim 11, wherein the spread of the prescribed administration object substance comprises an extent of diffusion of the prescribed administration object substance in a direction approximately parallel to a superficial layer of the prescribed object region.

13. The method according to claim 11, wherein the distribution information further comprises information regarding whether the prescribed administration object substance is to be directly introduced into a cell or the prescribed administration object substance is to be diffused between cells when administering the prescribed administration object substance to the prescribed object region.

14. The method according to claim 11, wherein the configuration of the object administration apparatus comprises at least one of a type of the gunpowder, an amount of the gunpowder configured to be loaded into the object administration apparatus, a shape of an ignition charge, or a presence or absence of a gas generating agent.

15. A system for calculating design specifications of a medical apparatus configured to perform a prescribed medical operation on an object region using a high-energy substance as a driving source, the system comprising:
    an apparatus specification unit configured to specify the medical apparatus for which the design specifications are to be calculated, as an object medical apparatus;
    a first acquisition unit configured to acquire operation information related to the prescribed medical operation to be performed in the object medical apparatus;
    a second acquisition unit configured to acquire region information related to a prescribed object region in which the prescribed medical operation is to be performed, the region information comprising at least one of a thickness, a density or a Poisson's ratio of the prescribed object region, or a relaxation time of a stress in the prescribed object region;
    a third acquisition unit configured to acquire change information related to a change in the prescribed object region, the change being anticipated to occur in the prescribed object region when the prescribed medical operation is performed by the object medical apparatus; and
    a calculation unit configured to calculate, based on the operation information acquired by the first acquisition unit, the region information acquired by the second acquisition unit, and the change information acquired by the third acquisition unit, design specification information related to a configuration of the object medical apparatus including energy information related to the high-energy substance to be used for the prescribed medical operation.

16. The system according to claim 15, wherein the stress comprises shear stress and compressive stress in the prescribed object region.

17. The system according to claim 15, wherein the prescribed object region includes a plurality of layers formed in a direction of administering an administration object substance, and wherein the region information comprises information related to a layer structure of the prescribed object region.

18. The system according to claim 15, wherein the high-energy substance comprises gunpowder, and wherein the configuration of the object medical apparatus comprises at least one of a type of the gunpowder, an amount of the gunpowder configured to be loaded into the object medical apparatus, a shape of an ignition charge, or a presence or absence of a gas generating agent.

* * * * *